(12) United States Patent
Iwakiri et al.

(10) Patent No.: US 9,265,476 B2
(45) Date of Patent: Feb. 23, 2016

(54) RADIATION IMAGING SYSTEM AND RADIATION IMAGING DEVICE

(71) Applicant: FUJIFILM Corporation, Tokyo (JP)

(72) Inventors: Naoto Iwakiri, Kanagawa-ken (JP); Naoyuki Nishino, Kanagawa-ken (JP); Yasunori Ohta, Kanagawa-ken (JP); Haruyasu Nakatsugawa, Kanagawa-ken (JP)

(73) Assignee: FUJIFILM CORPORATION, Tokyo (JP)

( * ) Notice: Subject to any disclaimer, the term of this patent is extended or adjusted under 35 U.S.C. 154(b) by 50 days.

(21) Appl. No.: 13/753,210

(22) Filed: Jan. 29, 2013

(65) Prior Publication Data

US 2013/0142309 A1 Jun. 6, 2013

Related U.S. Application Data

(63) Continuation of application No. PCT/JP2011/069153, filed on Aug. 25, 2011.

(30) Foreign Application Priority Data

Aug. 27, 2010 (JP) ................................. 2010-191467
Aug. 27, 2010 (JP) ................................. 2010-191468

(51) Int. Cl.
*H05G 1/54* (2006.01)
*A61B 6/00* (2006.01)

(52) U.S. Cl.
CPC ............... *A61B 6/586* (2013.01); *A61B 6/4233* (2013.01); *A61B 6/4283* (2013.01); *A61B 6/4452* (2013.01); *A61B 6/54* (2013.01); *A61B 6/56* (2013.01)

(58) Field of Classification Search
CPC ................................ A61B 6/102; A61B 6/585
USPC ......................................................... 378/117
See application file for complete search history.

(56) References Cited

U.S. PATENT DOCUMENTS 7,046,764 B1 * 5/2006 Kump ........................... 378/117
2010/0091945 A1 4/2010 Kotani

FOREIGN PATENT DOCUMENTS

JP 2005-177379 A 7/2005
JP 2006-339752 A 12/2006
JP 2010-094196 4/2010

OTHER PUBLICATIONS

Rejection of the Application issued by JPO on Apr. 8, 2014 in connection with corresponding Japanese Patent Application No. 2010-191467.

(Continued)

*Primary Examiner* — Hoon Song
(74) *Attorney, Agent, or Firm* — Jean C. Edwards, Esq.; Edwards Neils PLLC

(57) ABSTRACT

A radiation imaging system that can continuously use sections of a radiation imaging device that has not been damaged and a radiation imaging device are provided. The radiation imaging system comprises: a radiation device that applies radiation; and the radiation imaging device with an imaging panel that captures images of the applied radiation. The radiation imaging device comprises: a failure cause detection unit that detects environmental noise or falls that cause failures in the radiation imaging device; a malfunction diagnostic unit that, in a case where a detected environmental noise value reaches a threshold value or in a case where a fall has been detected, diagnoses a malfunction in the radiation imaging device; and a function limiting unit that applies limits to the radiation imaging device functions that are used continuously, in accordance with the diagnosis results of the malfunction diagnostic unit.

12 Claims, 16 Drawing Sheets

(56) References Cited

OTHER PUBLICATIONS

Rejection of the Application issued by JPO on Apr. 8, 2014 in connection with corresponding Japanese Patent Application No. 2010-191468.

Chinese First Office Action, issued by the State Intellectual Property Office of China on Oct. 30, 2014 in the corresponding Chinese Patent Application No. 201180037650.8.

Rejection of the Application, issued by the Japanese Patent Office on Dec. 2, 2014, in the corresponding Japanese Patent Application No. 2010-191468.

\* cited by examiner

RADIATION IMAGING SYSTEM AND RADIATION IMAGING DEVICE

CROSS-REFERENCE TO RELATED APPLICATIONS AND PRIORITY CLAIMS

This application is a Continuation of International Application No. PCT/JP2011/069153 filed on Aug. 25, 2011, which was published under PCT Article 21(2) in Japanese, which is based upon and claims the benefit of priority from Japanese Patent Application No. 2010-191467 filed on Aug. 27, 2010, and No. 2010-191468 filed on Aug. 27, 2010, the contents all of which are incorporated herein by reference.

TECHNICAL FIELD

The present invention relates to a radiographic image capturing system (radiation imaging system) and a radiographic image capturing apparatus (radiation imaging device) for capturing a radiographic image of a human body from radiation that has passed through the human body.

BACKGROUND ART

In the medical field, portable radiographic image capturing apparatus (e.g., FPD (Flat Panel Detector)) have been used for capturing a radiographic image of interior portions of a human body by detecting the intensity of radiation that has passed through the human body. Since the user of a portable FPD carries the portable FPD, the user may mistakenly drop the portable FPD or hit the portable FPD against a hard object such as an image capturing base, a door, or the like while handling the portable FPD, which could possibly cause damage to the portable FPD.

Japanese Laid-Open Patent Publication No. 2005-177379 discloses a portable FPD equipped with an impact sensor. The portable FPD initiates a self-diagnostic process in response to a signal from the impact sensor. If it is decided that the portable FPD has a fault based on the results of the self-diagnostic process, then the portable FPD is prohibited from starting an image capturing process or applying radiation to a target subject.

SUMMARY OF INVENTION

According to Japanese Laid-Open Patent Publication No. 2005-177379, in a case where a portable FPD has suffered from a fault, the portable FPD can no longer be used continuously. If there is only one FPD in a hospital and the FPD is found to be faulty, then medical examination processes in the hospital tend to be adversely affected due to the FPD being out of service. It is quite economically burdensome for the hospital to replace the FPD with a new one, which is highly expensive to purchase, each time that the FPD becomes defective.

Occasionally, the user drops the FPD inadvertently, however, a defect is not detected in the FPD at that time. In such a case, the FPD may possibly start to deteriorate from the moment it was dropped. According to Japanese Laid-Open Patent Publication No. 2005-177379, however, FPD deterioration that develops over time cannot be properly diagnosed.

The present invention has been made in view of the above problems of the background art. It is an object of the present invention to provide a radiographic image capturing system and a radiographic image capturing apparatus, which allow an undamaged section of the radiographic image capturing apparatus to be used continuously. Another object of the present invention is to provide a radiographic image capturing system and a radiographic image capturing apparatus, which are capable of accurately diagnosing deterioration that develops over time.

According to a first invention, there is provided a radiographic image capturing system having a radiation device for applying radiation and a radiographic image capturing apparatus including an image capturing panel for capturing an image from the applied radiation, wherein the radiographic image capturing apparatus comprises a fault factor detector for detecting an environmental disturbance or dropping, which is responsible for a fault of the radiographic image capturing apparatus, a fault diagnosing section for performing a diagnostic process to diagnose the radiographic image capturing apparatus for a fault if the detected environmental disturbance is equal to or greater than a threshold value or dropping is detected, and a function limiter for limiting a function of the radiographic image capturing apparatus, which is in continuous use, depending on the results of the diagnostic process performed by the fault diagnosing section.

The fault diagnosing section may include a self-diagnosing section for self-diagnosing the radiographic image capturing apparatus, wherein the self-diagnosing section diagnoses an entire image capturing area of the image capturing panel for a first unimageable region in which an image cannot be captured from the radiation, and the function limiter limits a function of the radiographic image capturing apparatus so as not to capture an image in the first unimageable region.

The self-diagnosing section may include a function to diagnose interconnections, and the function limiter may limit a function of the radiographic image capturing apparatus by preventing current from flowing into an interconnection that is diagnosed as being not normal.

The fault diagnosing section may include a real-image diagnosing section for diagnosing a second unimageable region in which an image cannot be captured from the radiation based on image data captured by an idle exposure process. The radiation device may apply diagnostic radiation for diagnosing the radiographic image capturing apparatus to the image capturing panel if the environmental disturbance detected by the fault factor detector is equal to or greater than the threshold value or dropping is detected by the fault factor detector. The real-image diagnosing section may diagnose the second unimageable region based on image data generated from the diagnostic radiation in the idle exposure process, and the function limiter may limit a function of the radiographic image capturing apparatus so as not to capture an image in the second unimageable region.

The radiographic image capturing system may further comprise an indicator for indicating, to a user, the results of the diagnostic process performed by the fault diagnosing section or the function limited by the function limiter.

The radiation device may inhibit image-capturing radiation from being applied until the diagnostic process performed by the fault diagnosing section is finished.

The environmental disturbance may comprise any one of an external pressure applied to the image capturing panel, an environmental temperature or a change therein, and an environmental humidity.

The radiographic image capturing apparatus may comprise a portable radiographic image capturing apparatus.

The radiographic image capturing apparatus may include a communication unit for sending a signal to and receiving a signal from another device through a wireless link. The self-diagnosing section may diagnose a communication function of the communication unit, and the function limiter may limit the communication function of the communication unit if the self-diagnosing section diagnoses the communication function of the communication unit as being abnormal.

The radiographic image capturing apparatus may include a storage unit for storing image data generated from the radiation. The self-diagnosing section may diagnose the storage unit, and the function limiter may limit a successive image capturing function if the storage unit has an available storage capacity smaller than a predetermined value.

The radiographic image capturing apparatus may include a built-in battery. The self-diagnosing section may diagnose the built-in battery, and the function limiter may limit use of the built-in battery if the built-in battery has a remaining stored energy level smaller than a predetermined value or a degree of deterioration greater than a predetermined value.

According to a second invention, there is provided a radiographic image capturing system having a radiation device for applying radiation, and a radiographic image capturing apparatus including an image capturing panel for capturing an image from the applied radiation, wherein the radiographic image capturing apparatus comprises a fault factor detector for detecting an environmental disturbance or dropping, which is responsible for a fault of the radiographic image capturing apparatus, and a fault diagnosing section for diagnosing an entire image capturing area of the image capturing panel for an unimageable region in which an image cannot be captured from the radiation, if the detected environmental disturbance is equal to or greater than a threshold value or dropping is detected, and wherein the radiographic image capturing system includes an indicator for indicating, to a user, the unimageable region if the unimageable region is diagnosed as being present within the entire image capturing area.

According to a third invention, there is provided a radiographic image capturing apparatus comprising a fault factor detector for detecting an environmental disturbance or dropping, which is responsible for a fault of the radiographic image capturing apparatus, a fault diagnosing section for performing a diagnostic process to diagnose the radiographic image capturing apparatus for a fault if the detected environmental disturbance is equal to or greater than a threshold value or dropping is detected, and a function limiter for limiting a function of the radiographic image capturing apparatus depending on the results of the diagnostic process performed by the fault diagnosing section.

According to the first through third inventions, if the environmental disturbance is equal to or greater than a threshold value or if dropping is detected, the radiographic image capturing apparatus is diagnosed for a fault, and a function of the radiographic image capturing apparatus is limited. Therefore, the radiographic image capturing apparatus, which suffers from the fault, can still be used continuously. Since a function of the radiographic image capturing apparatus is limited depending on the fault, the radiographic image capturing apparatus is prevented from becoming unduly heated, and electric power consumption is minimized.

According to a fourth invention, there is provided a radiographic image capturing system having a radiation device for applying radiation, and a radiographic image capturing apparatus including an image capturing panel for capturing an image from the applied radiation, wherein the radiographic image capturing apparatus comprises a fault diagnosing section for performing a first fault diagnosing process to periodically diagnose the radiographic image capturing apparatus for a fault, and a fault factor detector for detecting an external pressure or dropping of the radiographic image capturing apparatus, wherein if the detected external pressure is equal to or greater than a threshold value or dropping of the radiographic image capturing apparatus is detected, the fault diagnosing section performs the first fault diagnosing process, and periodically performs the first fault diagnosing process at shortened intervals.

The first fault diagnosing process may include a function to diagnose an entire image capturing area of the image capturing panel for an unimageable region in which an image cannot be captured from the radiation, based on image data generated by an idle exposure process or a blank reading process. The radiation device may apply diagnostic radiation for diagnosing the radiographic image capturing apparatus for a fault in the image capturing panel when the first fault diagnosing process is performed, and the first fault diagnosing process performed by the fault diagnosing section may diagnose the unimageable region based on image data generated from the diagnostic radiation by the idle exposure process.

If the detected external pressure is equal to or greater than the threshold value or dropping of the radiographic image capturing apparatus is detected, the fault diagnosing section may subsequently periodically perform a second fault diagnosing process along with the first fault diagnosing process.

The second fault diagnosing process may include a function to diagnose a resolution of an image based on image data generated by the idle exposure process using a resolution test chart.

The radiographic image capturing system may further comprise an indicator for indicating, to a user, the results of the first fault diagnosing process performed by the fault diagnosing section.

If the external pressure, an environmental humidity, an environmental temperature, or a change in the environmental temperature is equal to or greater than a predetermined value, or if the number of times that the external pressure, the environmental humidity, the environmental temperature, or a change in the environmental temperature is equal to or greater than the predetermined value exceeds a predetermined number, the fault diagnosing section may periodically perform the first fault diagnosing process at shortened intervals.

The radiographic image capturing system may further comprise a function limiter for limiting a function of the radiographic image capturing apparatus based on the results of the first fault diagnosing process performed by the fault diagnosing section.

The radiographic image capturing apparatus may comprise a portable radiographic image capturing apparatus.

The radiation device may inhibit image-capturing radiation from being applied while the first fault diagnosing process is being performed by the fault diagnosing section.

According to a fifth invention, there is provided a radiographic image capturing apparatus comprising a fault diagnosing section for performing a first fault diagnosing process to periodically diagnose the radiographic image capturing apparatus for a fault, and a fault factor detector for detecting an external force or dropping of the radiographic image capturing apparatus, wherein the fault diagnosing section performs the first fault diagnosing process, and periodically performs the first fault diagnosing process at shortened intervals if the detected external force is equal to or greater than a threshold value or dropping is detected.

According to the fourth and fifth inventions, the first fault diagnosing process is periodically performed, and if the external force is equal to or greater than a threshold value or if dropping is detected, then the first fault diagnosing process is performed, and intervals at which the first fault diagnosing process is periodically performed are shortened. Consequently, the degree to which the radiographic image capturing apparatus deteriorates over time can accurately be diagnosed, thereby making it possible to predict a time at which a replacement radiographic image capturing apparatus should be purchased, as well as predicting a time at which parts of the radiographic image capturing apparatus should be replaced.

BRIEF DESCRIPTION OF DRAWINGS

FIGS. 4A and 4B are schematic views of different structures of a radiation detector shown in FIG. 3, in which FIG. 4A shows a radiation detector with a scintillator formed on an aluminum substrate by vacuum evaporation, and FIG. 4B shows a radiation detector with a scintillator formed on a TFT substrate by vacuum evaporation;

DESCRIPTION OF EMBODIMENTS

A radiographic image capturing system, which includes therein radiographic image capturing apparatus according to preferred embodiments of the present invention, will be described in detail below with reference to the accompanying drawings.

First Embodiment

Figure 1:
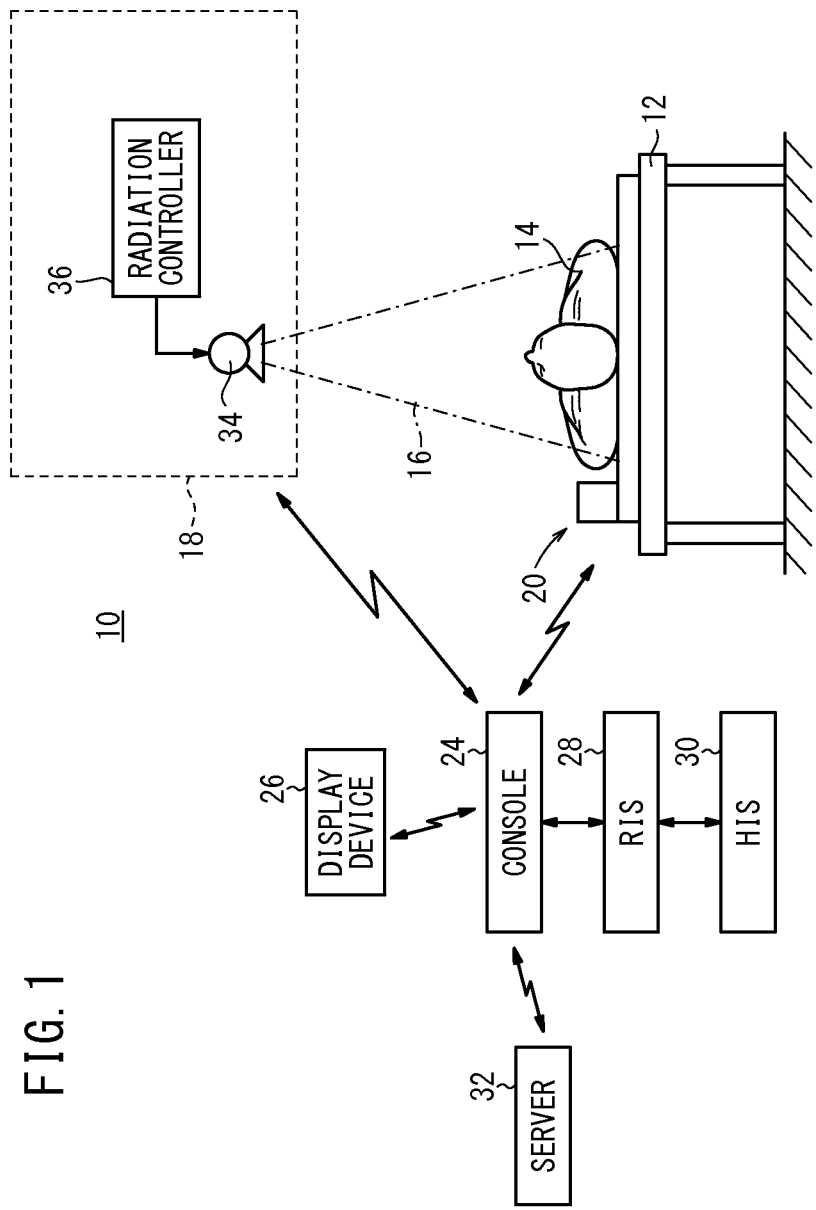
FIG. 1 is a view showing a configuration of a radiographic image capturing system according to a first embodiment of the present invention.

FIG. 1 is a view showing a configuration of a radiographic image capturing system 10 according to a first embodiment of the present invention. The radiographic image capturing system 10 includes a radiation device 18 for applying radiation 16 to a patient as a subject 14 lying on an image capturing base 12 such as a bed or the like, an electronic cassette (radiographic image capturing apparatus) 20 for detecting radiation 16 that has passed through the subject 14 and converting the detected radiation into a radiographic image, a console 24 for controlling the radiographic image capturing system 10 in its entirety, and a display device 26 for displaying a captured radiographic image, etc. The console 24 has an input unit for receiving input actions entered by a doctor or a radiological technician (hereinafter referred to as a "user").

The console 24, the radiation device 18, the electronic cassette 20, the display device 26, and a server 32 send and receive signals through a wireless LAN such as UWB (Ultra-Wide Band), IEEE802.11.a/b/g/n, or the like, or through a wireless communication link using milliwaves, or the like. Alternatively, the console 24, the radiation device 18, the electronic cassette 20, the display device 26, and the server 32 may send and receive signals through a wired communication link including cables.

The console 24 is connected to a radiology information system (RIS) 28, which generally manages radiographic image information handled by the radiological department of a hospital, together with other information. The RIS 28 is connected to a hospital information system (HIS) 30, which generally manages medical information in the hospital.

The server 32, which is connected to the console 24 by a wireless communication link, is provided on the premises of a maintenance provider. The console 24 sends the results of a diagnostic process, to be described later, performed on the electric cassette 20 to the server 32, so that the maintenance provider can grasp the status of the electronic cassette 20.

The radiation device 18 has a radiation source 34 for applying radiation 16, and a radiation controller 36 for controlling the radiation source 34. The radiation source 34 applies radiation 16 to the electronic cassette 20. Radiation 16 applied by the radiation source 34 may be in the form of X-rays, α rays, β rays, γ rays, an electron beam, or the like.

Figure 2:
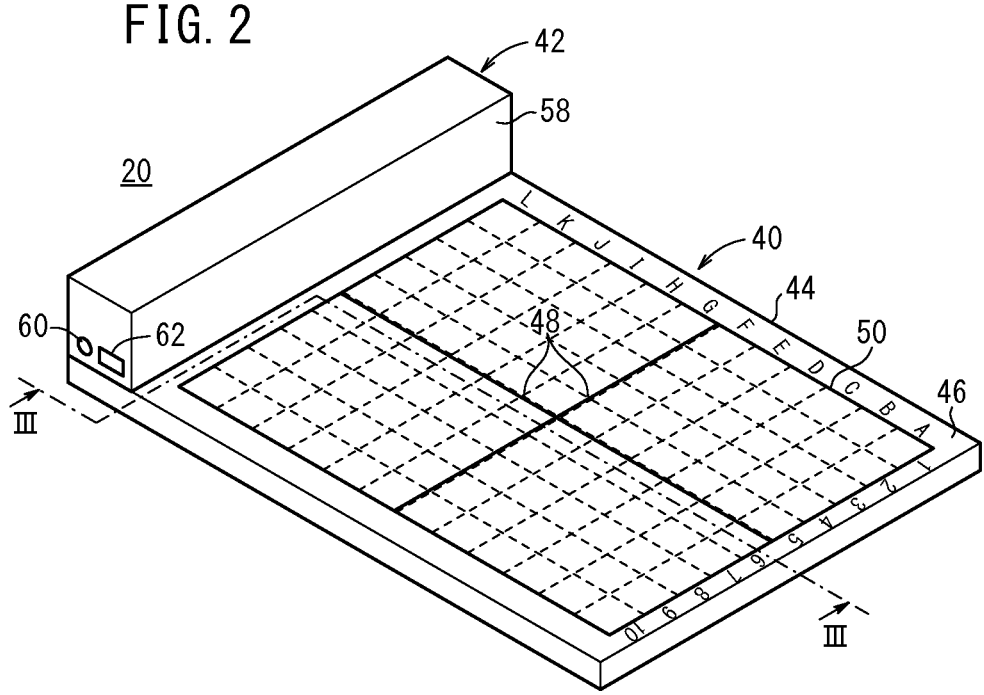
FIG. 2 is a perspective view of an electronic cassette shown in FIG. 1.
Figure 3:
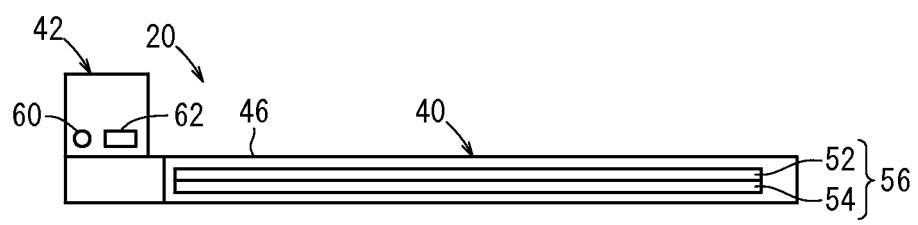
FIG. 3 is a cross-sectional view taken along line III-III of FIG. 2.

FIG. 2 is a perspective view of the electronic cassette 20 shown in FIG. 1, and FIG. 3 is a cross-sectional view taken along line III-III of FIG. 2. The electronic cassette 20 includes a panel unit (image capturing panel) 40, and a controller 42 disposed on the panel unit 40. The panel unit 40 is thinner than the controller 42.

The panel unit 40 includes a substantially rectangular housing 44 made of a material that is permeable to radiation 16. The panel unit 40 has an image capturing surface 46, which is irradiated with radiation 16. The image capturing surface 46 includes guide lines 48 disposed substantially centrally thereon. The guide lines 48 are indicative of an image capturing area and an image capturing position for the subject 14. The guide lines 48 include an outer frame representing an imageable region 50, which indicates an irradiation field to be irradiated with radiation 16. The guide lines 48 have a central position (where two guide lines 48 cross each other in a crisscross pattern), which serves as the central position of the imageable region 50. The image capturing surface 46 is marked with area graduations indicative of the image capturing area. The area graduations include numerals (1, 2, . . . ) representing columns, and alphabetical letters (A, B, . . . ) representing rows. A sheet and a seal, which are applied to the image capturing surface 46, and a storage bag for storing the electronic cassette 20 may also be marked with area graduations.

The panel unit 40 includes a radiation detector 56 having a scintillator 52 and a radiation conversion panel 54, and a driver circuit 80 (see FIG. 5) for energizing the radiation conversion panel 54. The scintillator 52 converts radiation 16 that has passed through the subject 14 into visible phosphorescence that exists within a visible light range. The radiation conversion panel 54 comprises an indirect conversion panel, which converts phosphorescence generated by the scintillator 52 into electric signals. The scintillator 52 and the radiation conversion panel 54 are disposed in the housing 44 so as to be arranged successively from the image capturing surface 46 that is irradiated with radiation 16. If the radiation conversion panel 54 comprises a direct conversion panel, which converts radiation 16 directly into electric signals, then since the scintillator 52 is not required, the radiation conversion panel 54 itself serves as the radiation detector 56.

The controller 42 has a substantially rectangular housing 58 made of a material impermeable to radiation 16. The housing 58 extends along one end of the image capturing surface 46 so that the controller 42 is disposed outside of the imageable region 50 on the image capturing surface 46. The housing 58 accommodates therein a cassette controller 84 for controlling the panel unit 40, a communication unit 88 for sending signals to and receiving signals from the console 24 through a wireless communication link, and a built-in battery 90, etc. (see FIG. 5). The built-in battery 90 supplies electric power to the cassette controller 84, the communication unit 88, etc. The controller 42 has a side surface on one longitudinal end thereof, which includes an input terminal 60 of an AC adapter for charging the built-in battery 90 from an external power supply, and an USB (Universal Serial Bus) terminal 62 that serves as an interface for sending information to and receiving information from an external apparatus (e.g., the console 24 or the like).

Figure 4A:
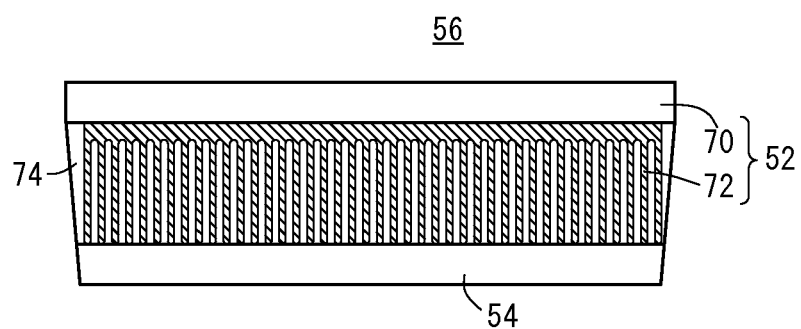
Figure 4B:
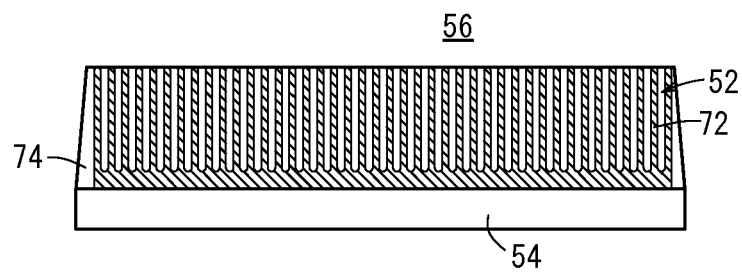

FIGS. 4A and 4B are schematic views of different structures of the radiation detector 56. FIG. 4A shows a radiation detector 56 including a scintillator 52, which is formed by vacuum evaporation on an aluminum substrate 70. FIG. 4B shows a radiation detector 56 including a scintillator 52, which is formed by vacuum evaporation on a TFT substrate.

As shown in FIG. 4A, the scintillator 52 has a strip-like columnar crystalline structure 72 made up of cesium iodide (CsI(Tl), which is formed on the aluminum substrate 70 by vacuum evaporation, for example. The radiation conversion panel 54 is disposed on one side of the columnar crystalline structure 72 remote from the aluminum substrate 70. The scintillator 52 and the radiation conversion panel 54 are held securely against each other. The radiation conversion panel 54 comprises a layer of pixels disposed on a TFT substrate. Since CsI having such a columnar crystalline structure 72 is susceptible to humidity (water) (especially, a non-columnar crystalline section of the scintillator 52 is susceptible to humidity), the scintillator 52 is sealed by a humidity-resistant protector 74. Relative positions of the scintillator 52 and the radiation conversion panel 54 are secured as a result of being held against each other. However, the scintillator 52 and the radiation conversion panel 54 may be bonded to each other to thereby secure the scintillator 52 and the radiation conversion panel 54.

As shown in FIG. 4B, the scintillator 52 has a strip-like columnar crystalline structure 72 made up of cesium iodide (CsI(Tl)), which is formed on the TFT substrate by vacuum evaporation. The scintillator 52 is sealed by a humidity-resistant protector 74. Since the columnar crystalline structure 72 is hard and brittle, the columnar crystalline structure 72 is susceptible to external pressure and stress. Therefore, if the electronic cassette 20 is dropped or is subjected to excessive external pressure, then the columnar crystalline structure 72 and the humidity-resistant protector 74 are liable to become cracked, and the columnar crystalline structure 72 is liable to break. Further, since the scintillator 52 and the TFT substrate have different coefficients of thermal expansion, a change in temperature tends to put the scintillator 52 under stress, thereby causing the columnar crystalline structure 72 and the humidity-resistant protector 74 to crack, and causing the columnar crystalline structure 72 to break. If the columnar crystalline structure 72 becomes cracked and the humidity-resistant protector 74 becomes broken, then not only are the image capturing performance and the sensitivity thereof lowered, but also a region is likely to occur in the radiation detector 56 in which radiographic images cannot be captured.

If the columnar crystalline structure 72 becomes cracked, then since the electronic cassette 20 is subject to stress (i.e., is placed under an external pressure or stress due to different coefficients of thermal expansion upon a temperature change) as a result of usage over time and changes in environmental temperature, the crack will grow over time, thereby causing the columnar crystalline structure 72 to break. Further, if the humidity-resistant protector 74 becomes cracked or fractured, then water enters through such cracks, etc., thereby causing the columnar crystalline structure 72 to deliquesce over time. Therefore, the image capturing performance and resolution of the radiation detector 56 are gradually lowered.

Figure 5:
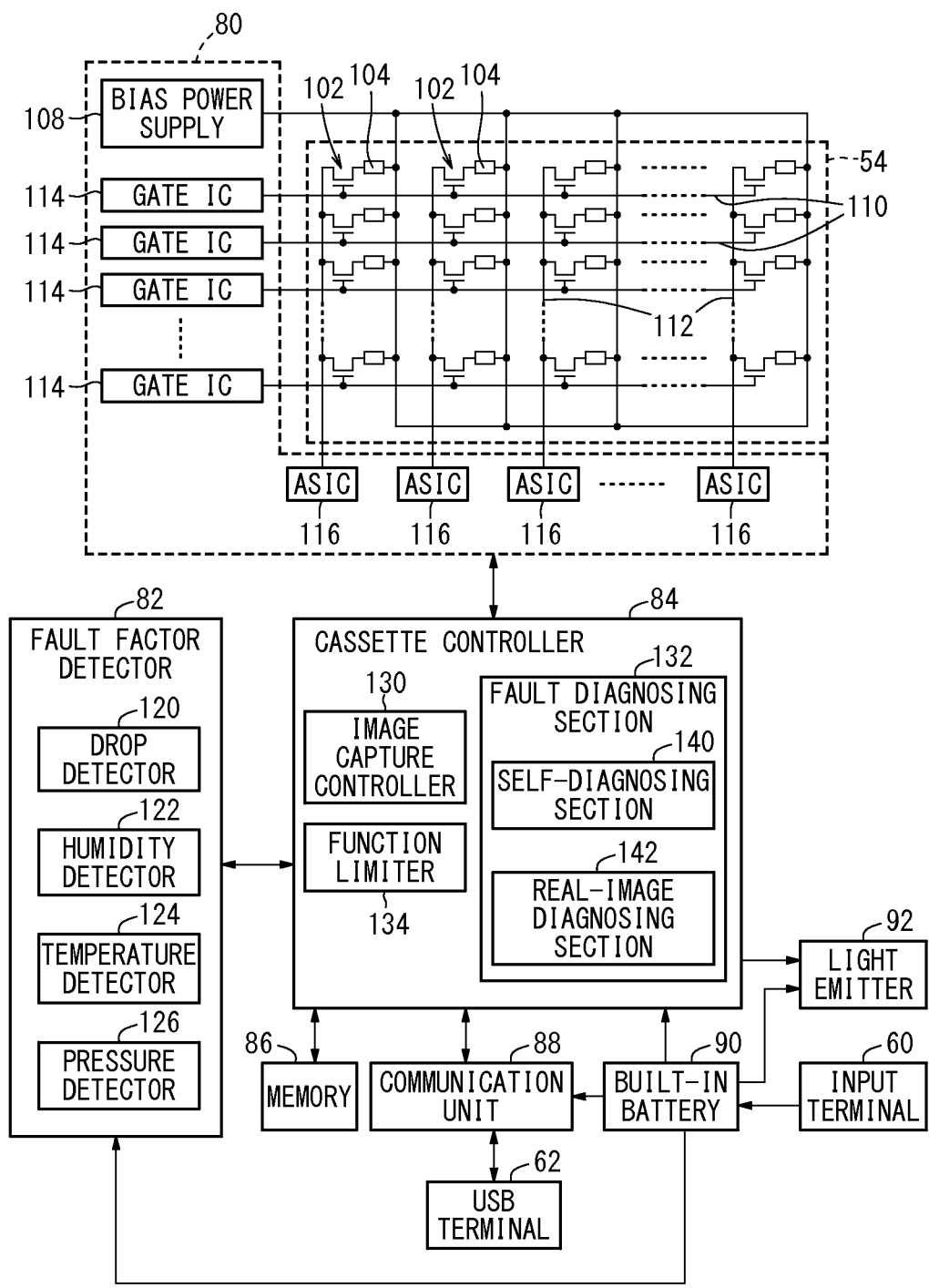
FIG. 5 is an electric block diagram of the electronic cassette shown in FIG. 1.

FIG. 5 is an electric block diagram of the electronic cassette 20 shown in FIG. 1. The electronic cassette 20 includes the driver circuit 80, a fault factor detector 82, the cassette controller 84, a memory (storage unit) 86, the communication unit 88, the built-in battery 90, and a light emitter (indicator) 92. The built-in battery 90 supplies electric power, respectively, to the fault factor detector 82, the cassette controller 84, the communication unit 88, and the light emitter 92. The cassette controller 84 supplies electric power, which was supplied thereto from the built-in battery 90, to a bias power supply 108, gate ICs (pixel drivers) 114, ASICs (pixel output circuits) 116, etc., and also judges whether or not the electric power from the built-in battery 90 should be supplied to the fault factor detector 82, the communication unit 88, and the light emitter 92, while controlling the amount of electric power that is supplied thereto.

The radiation conversion panel 54 comprises an array of TFTs 102, which are arranged in rows and columns, and a photoelectric conversion layer including plural pixels 104, which are disposed on the array of TFTs 102. The pixels 104, which are supplied with a bias voltage from the bias power supply 108 of the driver circuit 80, store electric charges therein, which are converted photoelectrically from phosphorescence generated by the scintillator 52.

To the TFTs 102, which are connected respectively to the pixels 104, gate lines 110 are connected that extend parallel to the rows, and signal lines 112 are connected that extend parallel to the columns. The gate lines 110 are connected to each of the gate ICs 114 of the driver circuit 80, whereas the signal lines 112 are connected to each of the ASICs 116 of the driver circuit 80.

In FIG. 5, one gate line 110 is shown as being connected to each of the gate ICs 114. Actually, however, multiple gate lines 110 are connected to each of the gate ICs 114. Plural pixels 104 are connected to each of the gate lines 110 through TFTs 102. In FIG. 5, one signal line 112 is shown as being connected to each of the ASICs 116. Actually, however, multiple signal lines 112 are connected to each of the ASICs 116. Plural pixels 104 are connected through TFTs 102 to each of the signal lines 112.

Each of the gate ICs 114 outputs gate signals to the gate lines 110. When the gate signals are output to the gate lines 110, the TFTs 102 connected to the gate lines 110 and to which the gate signals are output are simultaneously turned on, thereby reading electric charges stored in the pixels 104 through the TFTs 102 into the signal lines 112. Therefore, the electric charges stored in the pixels 104 are read from each row one at a time.

Upon each of the gate ICs 114 being supplied with a drive signal from the cassette controller 84, each of the gate ICs 114 successively selects the gate lines 110 connected thereto, and outputs gate signals to the selected gate lines 110, thereby successively reading electric charges stored in the pixels 104 from each row one at a time. After the gate IC 114 has output the gate signals to all of the gate lines 110 connected thereto, i.e., after the gate IC 114 has read all the electric charges stored in the pixels 104 that are capable of being read, the gate IC 114 outputs an end signal to the cassette controller 84.

Each of the ASICs 116 comprises an amplifier for amplifying the read electric charge signals (electric signals), a multiplexer, an A/D converter, etc. After having amplified the electric signals read from the signal lines 112, each of the ASICs 116 successively selects the amplified electric signals, converts the selected electric signals into digital signals, and outputs the digital signals to the cassette controller 84.

The fault factor detector 82 detects an environmental disturbance or dropping of the electronic cassette 20, which is responsible as a fault factor of the electronic cassette 20. An environmental disturbance refers to an environmental humidity, an environmental temperature, a change in the environmental temperature, and an external pressure. The environmental humidity, the environmental temperature, and the change in the environmental temperature will collectively be referred to as "environmental stimuli". If a possibility exists for the electronic cassette 20 to fail due to other disturbances apart from the environmental humidity, the environmental temperature, the change in the environmental temperature, and the external pressure, then the fault factor detector 82 may detect other fault factors.

More specifically, the fault factor detector 82 comprises a drop detector 120, including an acceleration sensor, a gyroscope, or the like, for detecting if the electronic cassette 20 is dropped, a humidity detector 122, including an electric-resistance or an electric-capacitance humidity sensor, for detecting an environmental humidity of the electronic cassette 20, i.e., the humidity of an environment in which the electronic cassette 20 is placed, a temperature detector 124 including a thermocouple, a thermistor, or an infrared temperature sensor, for detecting an environmental temperature of the electronic cassette 20, i.e., the temperature of an environment in which the electronic cassette 20 is placed, and a pressure detector 126 including a pressure sensor such as a pressure-sensitive element, which may be a semiconductor diaphragm, an electrostatic capacitance sensor, or a piezoelectric sensor, for detecting an external pressure applied to the electronic cassette 20. The fault factor detector 82 may be installed at any location within the electronic cassette 20. The temperature detector 124 may have a function to detect a change in temperature over a certain period of time, e.g., 24 hours, such as a temperature difference between a highest temperature and a lowest temperature, or a temperature difference between a present temperature and a temperature at an earlier time, e.g., 1 hour before the present time.

The cassette controller 84 includes an image capture controller 130, a fault diagnosing section 132, and a function limiter 134. The image capture controller 130 controls the manner in which an image is captured with radiation 16. More specifically, the image capture controller 130 controls the timing at which the radiation conversion panel 54 is exposed to radiation 16, and the time at which images are read from the radiation conversion panel 54. The image capture controller 130 controls the exposure start timing so as to be in synchronism with the start of application of radiation 16 from the radiation device 18, and also controls the exposure end timing so as to be in synchronism with the end of application of radiation 16 from the radiation device 18. The image capture controller 130 synchronizes the exposure start timing and the exposure end timing by way of wireless communications with the radiation device 18 via the console 24.

The image capture controller 130 controls reading of an image by selecting a gate IC 114 and outputting a drive signal to the selected gate IC 114. After outputting the drive signal to the selected gate IC 114 and subsequently receiving an end signal from the selected gate IC 114, the image capture controller 130 selects a next gate IC 114 and outputs a drive signal to the selected gate IC 114. In this manner, electric charges stored in all of the pixels 104 of the radiation conversion panel 54 are read successively one row at a time, i.e., an image is read from the radiation conversion panel 54. The cassette controller 84 stores in the memory 86 digital signals representing image data sent from the ASICs 116. The communication unit 88 sends the image data stored in the memory 86 as packets to the console 24.

The fault diagnosing section 132 includes a self-diagnosing section 140 and a real-image diagnosing section 142. The self-diagnosing section 140 diagnoses whether or not the bias power supply 108, the gate ICs 114, and the ASICs 116 are operating normally or fail to operate. For example, the self-diagnosing section 140 sends a test signal to the gate ICs 114 and the ASICs 116, and diagnoses whether or not the gate ICs 114 and the ASICs 116 fail to operate based on response signals sent from the gate ICs 114 and the ASICs 116.

The self-diagnosing section 140 also diagnoses whether or not interconnections in the electronic cassette 20 are normal, i.e., whether such interconnections are short-circuited, broken, or unstable (i.e., suffering from a contact failure representing a repetition of making and breaking circuits). Further, the self-diagnosing section 140 diagnoses an unimageable region in which a radiographic image cannot be captured from the radiation 16.

Figure 6:
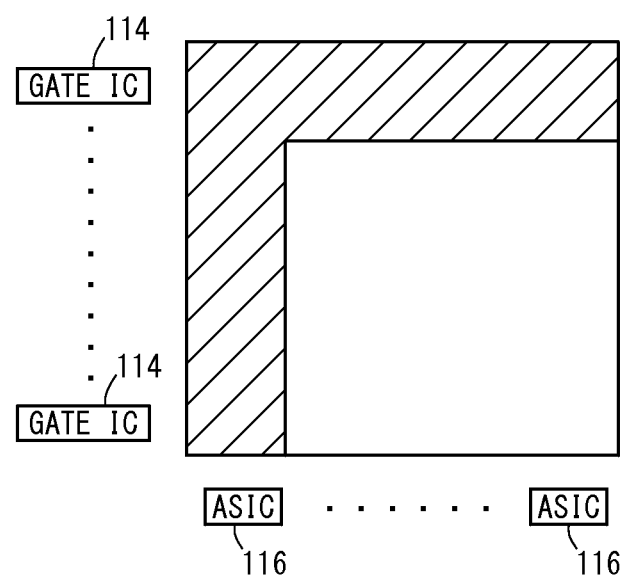
FIG. 6 is a diagram showing by way of example an unimageable region diagnosed by a self-diagnosing section.

FIG. 6 is a diagram showing by way of example an unimageable region included within the imageable region 50, which is diagnosed by the self-diagnosing section 140. As shown in FIG. 6, an uppermost one of the gate ICs 114 and a leftmost one of the ASICs 116 suffer from a failure due to broken or short-circuited interconnections, thereby producing an unimageable region, as shown in hatching. Since the faulty gate IC 114 is unable to output a gate signal to the connected gate lines 110, the faulty gate IC 114 is unable to read electric charges stored in the pixels 104, which are connected through the TFTs 102 to the gate lines 110. The unimageable region contains pixels 104 that are connected through the TFTs 102 to the gate lines 110, which are connected to the faulty gate IC 114.

The faulty ASIC 116 is unable to output electric charge signals sent to the cassette controller 84 from the signal lines 112 that are connected to the faulty ASIC 116. The unimageable region contains pixels 104 that are connected through the TFTs 102 to the signal lines 112, which are connected to the faulty ASIC 116.

The self-diagnosing section 140 also diagnoses the memory 86, the communication unit 88, and the built-in battery 90. For example, the self-diagnosing section 140 diagnoses the memory 86 for available storage capacity by checking if the memory 86 has any malfunctioning cells. The self-diagnosing section 140 also diagnoses the communication unit 88 for a communication function thereof by performing a communication test on the communication unit 88 for communication with the console 24. The self-diagnosing section 140 also diagnoses the built-in battery 90 for a remaining stored energy level (capacity) and a degree of deterioration of the built-in battery 90 based on the charged voltage of the built-in battery 90, which is detected by a voltage sensor combined with the built-in battery 90. The self-diagnosing section 140 may also carry out a load current test in order to diagnose the built-in battery 90 for the remaining stored energy level and the degree of deterioration thereof.

The real-image diagnosing section 142 performs a real-image diagnostic process for diagnosing an unimageable region, which is unable to capture an image, based on image data generated by an idle exposure process. In the idle exposure process, the electronic cassette 20 is directly exposed to radiation 16 that actually is applied thereto. More specifically, even if a region of the imageable region 50 is diagnosed as not being an unimageable region by the real-image diagnosing section 142, the region may not actually be capable of capturing an image. For example, since a region where the columnar crystalline structure 72 of the scintillator 52 is broken is unable to convert radiation 16 into phosphorescence, such a region is incapable of capturing an image from the radiation 16. Further, if relative positions of the scintillator 52 and the radiation conversion panel 54 are shifted, then the imageable region 50 may contain a region in which the phosphorescence generated by the scintillator 52 is not applied, whereby such a region is not capable of capturing an image from the radiation 16. The idle exposure process refers to a process in which an image is captured from radiation 16 that is applied from the radiation device 18 to the electronic cassette 20 during a time that a subject 14 is not present between the radiation device 18 and the electronic cassette 20.

The real-image diagnosing section 142 may diagnose, as an unimageable region, a region made up of a striped pattern or a web-like pattern of detected values, which are significantly different from those in a surrounding region. Furthermore, since the image capturing conditions for the idle exposure process are predetermined, values of image data generated by the idle exposure process may be expected to fall within a certain range. Therefore, the real-image diagnosing section 142 may diagnose, as an unimageable region, a region that is made up of image data outside of the certain range. More specifically, the radiation device 18 applies diagnostic radiation 16, and the image capture controller 130 controls capturing of an image with the applied diagnostic radiation 16. The real-image diagnosing section 142 diagnoses the imageable region 50 for an unimageable region based on image data of the image captured from the diagnostic radiation 16. If the image capture controller 130 controls capturing of an image with the applied diagnostic radiation 16, the timing at which the diagnostic radiation 16 starts to be applied and the exposure start timing need not be in synchronism with each other, insofar as an image can be captured from the diagnostic radiation 16.

The function limiter 134 limits functions of the electronic cassette 20 during continuous use thereof depending on the results of a fault diagnosing process carried out by the fault diagnosing section 132. For example, if the self-diagnosing section 140 diagnoses a gate IC 114 or an ASIC 116 as being faulty, then the function limiter 134 inhibits electric power from being supplied to the faulty gate IC 114 or the faulty ASIC 116. Therefore, the faulty gate IC 114 or the faulty ASIC 116 is prevented from becoming unduly heated, and an unimageable region corresponding to the faulty gate IC 114 or the faulty ASIC 116 is limited, i.e., is prevented from being used in the image capturing process. In addition, the function limiter 134 stops supplying an electric current to an interconnection, which may be broken or short-circuited, which has been diagnosed as malfunctioning by the self-diagnosing section 140. Thus, the broken or short-circuited interconnection is prevented from generating heat. Since unwanted electric current is not supplied to the broken or short-circuited interconnection, electric power consumption of the electronic cassette 20 is minimized. Further, if a gate IC 114 is diagnosed as malfunctioning, a drive current may be inhibited from being supplied to the malfunctioning gate IC 114.

The function limiter 134 also limits functions of the electronic cassette 20 so as not to acquire an image from an unimageable region that has been diagnosed by the real-image diagnosing section 142. For example, the electric charges stored in pixels 104 that are diagnosed as making up an unimageable region are not read from such pixels 104. More specifically, electric power is inhibited from being supplied to the gate ICs 114 for reading the stored electric charges from pixels 104 in the unimageable region, or is inhibited from being supplied to the ASICs 116 for outputting electric charges stored in pixels 104 in the unimageable region as digital signals. Further, gate signals are inhibited from being output to the gate lines 110 for reading the electric charges stored in pixels 104 in the unimageable region. Since an image capturing process is not performed in the unimageable region, an image is not acquired from the unimageable region.

Since each of the gate ICs 114 reads electric charges stored in pixels 104 along a plurality of rows, if such pixels 104 include even one pixel belonging to an unimageable region, then the electric charges stored in all of such pixels 104 along the rows cannot be read. Therefore, if the ratio of the number of pixels 104 in the unimageable region to the number of pixels 104 outside of the unimageable region, from among all of the pixels 104 to be read by a gate IC 114 that reads the electric charges stored in the pixels 104 in the unimageable region, is equal to or greater than a prescribed ratio, electric power may be inhibited from being supplied to the gate IC 114, thereby preventing electric charges from being read from the pixels 104. This is because if the ratio of the number of pixels 104 in the unimageable region to the number of pixels 104 outside of the unimageable region is equal to or greater than the prescribed ratio, a good image cannot be acquired from the read electric charges. The same holds true for the ASICs 116. If the gate lines 110 are connected respectively to the gate ICs 114 whereas the signal lines 112 are connected respectively to the ASICs 116, then the above problem does not occur.

Even if the ratio of the number of pixels 104 in an unimageable region to the number of pixels 104 outside the unimageable region, among all of the pixels 104 to be read by a gate IC 114 that reads the electric charges stored in the pixels 104 in the unimageable region, is smaller than the prescribed ratio, electric power may be inhibited from being supplied to the gate IC 114, thereby preventing electric charges from being read from the pixels 104, provided that a certain number of pixels 104 or more are disposed in succession in the unimageable region. This is because if a certain number of pixels 104 or more are disposed in succession in the unimageable region, the region in which an image cannot be captured is too large to acquire a good image from the read electric charges. The same also holds true for the ASICs 116.

If electric charges stored in the pixels 104 are not inhibited from being read, then an image correcting process such as a pixel interpolation process may be carried out in order to eliminate the unimageable region. Such an image correcting process may be performed by the console 24 or the cassette controller 84. However, the image correcting process should not be carried out excessively, because if the image correcting process is excessive, then a disease diagnosis based on an image generated by the image correcting process tends to suffer from reduced accuracy. For example, if the shape or size of a lesion in a cancer diagnosis is measured based on an image generated by the electronic cassette 20, then the prescribed ratio or the certain number referred to above may be reduced in order to provide stricter conditions for inhibiting electric power from being supplied to the gate IC 114, or to prevent electric charges from being read from the pixels 104.

Rather than inhibiting electric power from being supplied to gate ICs 114 or ASICs 116, image data generated from image capturing radiation 16 may be trimmed in order to remove image data in a diagnosed unimageable region, thereby limiting the image capturing area. Therefore, image data generated from the imaging radiation 16 is free of image data that occurs within the unimageable region. Such trimmed image data may be stored in the memory 86 and sent to the console 24 by way of the communication unit 88. The image capturing radiation 16 and the diagnostic radiation 16 may have identical or different irradiating conditions, including tube currents, tube voltages, and irradiation times. Since the diagnostic radiation 16 simply is used for diagnostic purposes, the diagnostic radiation 16 may be applied at a smaller dosage (mAs value) than the image capturing radiation 16.

If the self-diagnosing section 140 diagnoses the memory 86 as having an available storage capacity that is smaller than a predetermined value, then the function limiter 134 limits a successive image capturing function. If the self-diagnosing section 140 diagnoses the communication unit 88 as malfunctioning, then the function limiter 134 inhibits electric power from being supplied to the communication unit 88 so as to limit the communication function thereof. If the self-diagnosing section 140 diagnoses the built-in battery 90 as having a remaining stored energy level that is smaller than a predetermined value, or as having deteriorated beyond a predetermined degree, then the function limiter 134 limits usage of the built-in battery 90. The function limiter 134 may not immediately limit usage of the built-in battery 90, but may limit usage thereof upon elapse of a certain period of time, e.g., 5 minutes. The function limiter 134 may not completely limit usage of the built-in battery 90, i.e., may not completely stop supplying electric power from the built-in battery 90, but may limit the amount of electric power that is capable of being supplied from the built-in battery 90. The function limiter 134 may limit the amount of electric power supplied from the built-in battery 90 by reducing the number of devices or units to which electric power is supplied from the built-in battery 90.

If the wireless function of the communication unit 88 is limited, e.g., if electric power is inhibited from being supplied to the communication unit 88, then the user can connect the USB connector, which is on the tip end of a USB cable that is connected to the console 24, to the USB terminal 62, thereby interconnecting the electronic cassette 20 and the console 24 through a wired link. If electric power is inhibited from being supplied to the communication unit 88, then the malfunctioning communication unit 88 is prevented from becoming unduly heated. If the communication function of the communication unit 88 fails, then data intended to be sent to the console 24 are stored in the memory 86, and such stored data are sent to the console 24 after the electronic cassette 20 and the console 24 have been connected to each other by way of the USB cable. According to the first embodiment, the USB cable, which also doubles as a power supply cable, is used to establish a wired communication link between the electronic cassette 20 and the console 24. However, a communication cable, which does not double as a power supply cable, may be used instead of the USB cable.

If usage of the built-in battery 90 is limited, then the AC connector, which is provided on the tip end of a cable from an external power supply, may be connected to the input terminal 60 for thereby supplying electric power to the electronic cassette 20 from the external power supply. Accordingly, the electronic cassette 20 is protected from a sudden power shortage while it is in use.

The light emitter 92 emits light to thereby inform the user that certain functions of the communication unit 88 and the built-in battery 90 have been limited. The light emitter 92 includes a plurality of light-emitting elements having different colors, e.g., red, blue, etc. In a case where the function of the communication unit 88 is limited by the function limiter 134, the cassette controller 84 controls the light emitter 92 to energize the red light-emitting element, for example. In a case where the function of the built-in battery 90 is limited by the function limiter 134, the cassette controller 84 controls the light emitter 92 to energize the blue light-emitting element, for example. Therefore, the user can recognize which functions, from among the functions of the communication unit 88 and the built-in battery 90, have been limited.

The function limiter 134 normally sends information concerning the function that has been limited to the console 24 through the communication unit 88. However, if the function limiter 134 has limited the function of the communication unit 88, then the function limiter 134 sends information concerning the limited function to the console 24 after the electronic cassette 20 and the console 24 have been connected to each other by way of the USB cable.

Figure 7:
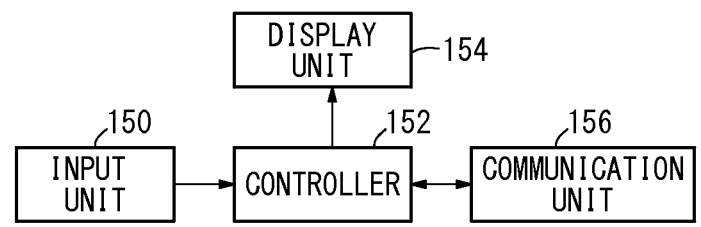
FIG. 7 is an electronic block diagram of a console shown in FIG. 1.

FIG. 7 is an electronic block diagram of the console 24. The console 24 includes an input unit 150 for receiving input signals entered by the user, a controller 152 for controlling the console 24 in its entirety, a display unit (indicator) 154, and a communication unit 156 for sending signals to and receiving signals from the electronic cassette 20, etc., through a wireless communication link. The controller 152 controls the display unit 154 to display the results of a diagnostic process performed by the fault diagnosing section 132 and to display the functions limited by the function limiter 134. Thus, the display unit 154 indicates the limited functions to the user.

Figure 8:
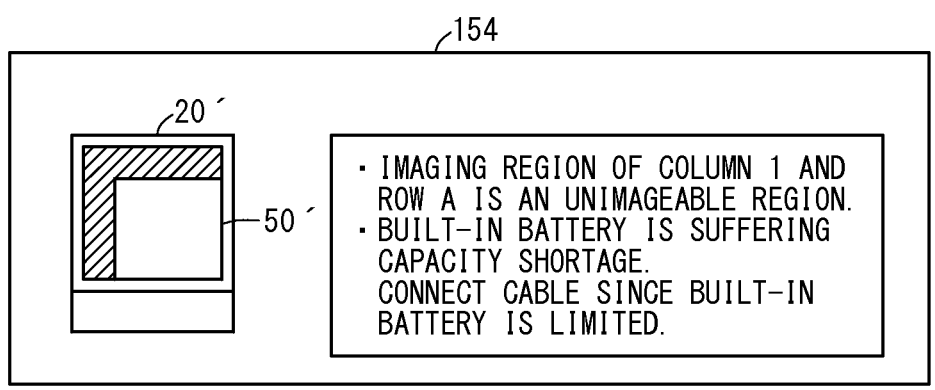
FIG. 8 is a view showing a displayed example of a function that is limited by a function limiter depending on the results of a self-diagnostic process.

FIG. 8 is a view showing a displayed example of a function, which is limited by the function limiter 134 depending on the results of a self-diagnostic process. According to the displayed example shown in FIG. 8, an image capturing area and a limitation of the built-in battery are displayed on the display unit 154. The display unit 154 displays an electronic cassette 20', which simulates the electronic cassette 20 as viewed from above, in a left-hand section of the screen, and also displays an explanation field for describing the limited functions in a right-hand section of the screen.

The electronic cassette 20', which is displayed on the display unit 154, has an imageable region 50' including a diagnosed (limited) unimageable region (shown in hatching). The explanation field displays a message "IMAGING REGION OF COLUMN 1 AND ROW A IS AN UNIMAGEABLE REGION." In this manner, the user can recognize which imaging region has been limited by observing the region graduations marked on the electronic cassette 20. The explanation field also displays a message "BUILT-IN BATTERY SUFFERS FROM A CAPACITY SHORTAGE. CONNECT CABLE SINCE BUILT-IN BATTERY IS LIMITED."

Figure 9:
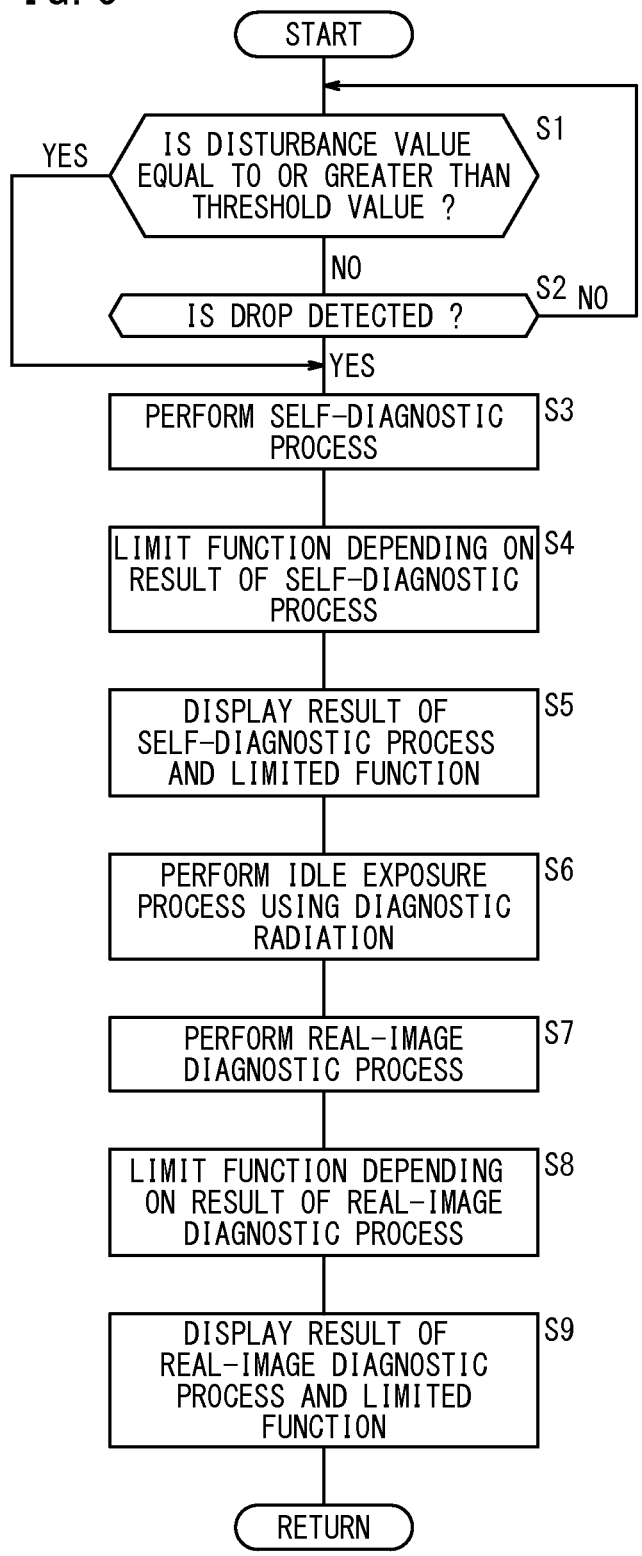
FIG. 9 is a flowchart of an operation sequence of the electronic cassette according to the first embodiment.

Operations of the electronic cassette 20 according to the first embodiment will be described below with reference to the flowchart shown in FIG. 9. The fault factor detector 82 periodically detects dropping of the electronic cassette 20 together with disturbance values (environmental humidity values, environmental temperature values, and external pressure values).

The fault diagnosing section 132 judges whether or not a detected disturbance value is equal to or greater than a threshold value (step S1). More specifically, the fault diagnosing section 132 judges whether or not any one of an environmental humidity value detected by the humidity detector 122, an environmental temperature value detected by the temperature detector 124, and an external pressure value detected by the pressure detector 126 is equal to or greater than a threshold value. Alternatively, the fault diagnosing section 132 may determine an evaluation value from the environmental humidity value detected by the humidity detector 122, the environmental temperature value detected by the temperature detector 124, or the external pressure value detected by the pressure detector 126, and judge whether or not the evaluation value is equal to or greater than a threshold value. Further, alternatively, the fault diagnosing section 132 may judge whether or not a temperature change detected by the temperature detector 124 is equal to or greater than a threshold value.

If the fault diagnosing section 132 decides that the disturbance value is not equal to or greater than the threshold value in step S1, then the fault diagnosing section 132 judges whether or not the drop detector 120 has detected dropping of the electronic cassette 20 or not (step S2). If the fault diagnosing section 132 decides that the drop detector 120 has not detected dropping of the electronic cassette 20, then control returns to step S1.

If the fault diagnosing section 132 decides that the disturbance value is equal to or greater than the threshold value in step S1, or if the fault diagnosing section 132 decides that the drop detector 120 has detected dropping of the electronic cassette 20 in step S2, then the self-diagnosing section 140 carries out a self-diagnostic process (step S3). More specifically, the self-diagnosing section 140 diagnoses the gate ICs 114 and the ASICs 116 for a fault, diagnoses the interconnections, and diagnoses the panel unit 40 for an unimageable region. Further, the self-diagnosing section 140 also diagnoses the memory 86, the communication unit 88, and the built-in battery 90. The self-diagnosing section 140 then sends the results of the self-diagnostic process to the console 24 through the communication unit 88. Until completion of the fault diagnosis (self-diagnostic process and real-image diagnostic process) of the electronic cassette 20, the cassette controller 84 sends an irradiation inhibition request to the console 24 through the communication unit 88 for inhibiting application of image-capturing radiation 16. The console 24 then sends an irradiation inhibition command to the radiation device 18. The radiation device 18 inhibits the radiation source 34 from applying image-capturing radiation 16 until the fault diagnosis is completed. If the communication unit 88 fails to operate, then since the console 24 cannot communicate with the electronic cassette 20 through the wireless communication link, the console 24 diagnoses the communication unit 88 as suffering from a fault, and inhibits image-capturing radiation 16 from being applied. The console 24 may inhibit image-capturing radiation 16 from being applied prior to step S3, or may start inhibiting image-capturing radiation 16 from being applied in step S4.

Then, the function limiter 134 limits functions of the electronic cassette 20, which is in continuous use, depending on the results of the self-diagnostic process in step S4. For example, if the self-diagnosing section 140 diagnoses a gate IC 114 or an ASIC 116 as suffering from a fault, then the function limiter 134 stops supplying electric power to the faulty gate IC 114 or to the faulty ASIC 116. Thus, an image capturing process in the unimageable region is limited. The function limiter 134 also stops supplying electric power to an interconnection, which has been diagnosed as being broken, short-circuited, or unstable. The function limiter 134 sends information to the console 24 through the communication unit 88 concerning the function that was limited depending on the results of the self-diagnostic process. The unimageable region, which is diagnosed by the self-diagnostic process, will be referred to as a first unimageable region.

Then, the controller 152 of the console 24 controls the display unit 154 to display the function that was limited depending on the results of the self-diagnostic process, as well as the function that was limited depending on the results of the self-diagnostic process (step S5). For example, if a gate IC 114 for reading the electric charges stored in the pixels 104 of the row indicated by a region corresponding to graduation A on the image capturing surface 46, and an ASIC 116 for reading the electric charges stored in the pixels 104 of the column indicated by a region corresponding to graduation 1 on the image capturing surface 46 are diagnosed as being faulty, then, as shown in FIG. 8, the diagnosed first unimageable region in the imageable region 50' of the electronic cassette 20' is displayed in hatching, and the message "IMAGING REGION OF COLUMN 1 AND ROW A IS AN UNIMAGEABLE REGION" is displayed in the explanation field. If the built-in battery 90 is diagnosed as having a remaining stored energy level lower than a predetermined value, then the message "BUILT-IN BATTERY IS SUFFERING FROM A CAPACITY SHORTAGE. CONNECT CABLE SINCE BUILT-IN BATTERY IS LIMITED" is displayed in the explanation field. If the function limiter 134 has limited the functions of the communication unit 88 and the built-in battery 90, then the function limiter 134 energizes the light emitter 92 to indicate the limited functions to the user.

Then, the image capture controller 130 performs an idle exposure process using diagnostic radiation 16 (step S6). More specifically, the image capture controller 130 outputs a request signal to the console 24 through the communication unit 88 for requesting application of diagnostic radiation 16. In response to the request signal, the console 24 outputs a command signal to the radiation device 18 for applying diagnostic radiation 16. In response to the command signal, the radiation device 18 applies diagnostic radiation 16. After having output the request signal, the image capture controller 130 controls the radiation conversion panel 54 so as to be exposed to diagnostic radiation 16 for a given period of time, and then reads the electric charges that are stored in the pixels 104 as a result of being exposed to diagnostic radiation 16. Image data that are converted from the electric charges generated as a result of being exposed to diagnostic radiation 16 are stored in the memory 86. At this time, image data are produced based on the diagnostic radiation 16, while the function is limited depending on the results of the self-diagnostic process.

Then, based on the image data, which are produced from the diagnostic radiation 16, the real-image diagnosing section 142 performs a real-image diagnostic process for diagnosing the electronic cassette 20 for an unimageable region in which an image cannot be captured (step S7). The unimageable region, which is detected by the real-image diagnosing section 142, is referred to as a second unimageable region. The real-image diagnosing section 142 sends the results of the real-image diagnostic process to the console 24 through the communication unit 88.

Then, the function limiter 134 limits the function of the electronic cassette 20, which is in continuous use, depending on the results of the real-image diagnostic process (step S8).

In other words, the function limiter 134 limits the function of the electronic cassette 20 so that an image will not be acquired from the unimageable region that is detected by the real-image diagnosing section 142. For example, the function limiter 134 may inhibit electric power from being supplied to gate ICs 114 and ASICs 116, so as not to read electric charges stored in the pixels 104 that belong to the diagnosed second unimageable region. Alternatively, image data generated based on the radiation 16 may be trimmed to remove image data from the second unimageable region. The function limiter 134 sends information to the console 24 through the communication unit 88 concerning the function that was limited depending on the results of the real-image diagnostic process.

Then, the controller 152 of the console 24 controls the display unit 154 to display the results of the real-image diagnostic process and the function that was limited depending on the results of the real-image diagnostic process (step S9). The controller 152 may control the display unit 154 to display the second unimageable region diagnosed by the real-image diagnostic process, in the same manner as shown in FIG. 8. If an image capturing area is limited by inhibiting electric power from being supplied to the gate ICs 114, which read the stored electric charges from the pixels 104 in the second unimageable region, then the actually limited image capturing area becomes wider than, and hence is not in agreement with, the second unimageable region. In this case, the actually limited image capturing area, rather than the second unimageable region, is displayed as an unimageable region. The function that was limited depending on the results of the real-image diagnostic process may be displayed along with the function that was limited depending on the results of the self-diagnostic process. For example, the first unimageable region and the second unimageable region may be displayed together. Upon completion of the fault diagnosing process, the cassette controller 84 sends a signal to the console 24 through the communication unit 88 indicating that image-capturing radiation 16 can be applied. The console 24 then sends a signal to the radiation device 18 indicating that image-capturing radiation 16 can be applied, whereby the image-capturing radiation 16 is made capable of applying the image-capturing radiation 16.

As described above, if an environmental disturbance value is equal to or greater than a threshold value or if dropping of the electronic cassette 20 is detected, then the electronic cassette 20 is diagnosed for a fault, and a function of the electronic cassette 20 is limited depending on the results of the diagnosis. Therefore, the electronic cassette 20, which has become faulty, can be used continuously. Since a function is limited depending on the fault, the electronic cassette 20 is prevented from becoming unduly heated, and hence electric power consumption is minimized.

If an environmental disturbance value is equal to or greater than a threshold value or if dropping of the electronic cassette 20 is detected, then the electronic cassette 20 is self-diagnosed for a first unimageable region in which an image cannot be captured from the radiation 16, and an image is not captured in the first unimageable region. Accordingly, the electronic cassette 20 is prevented from becoming unduly heated due to an image capturing process in the first unimageable region, and hence electric power consumption of the electronic cassette 20 is minimized.

If an environmental disturbance value is equal to or greater than a threshold value or if dropping of the electronic cassette 20 is detected, then the interconnections of the electronic cassette 20 are diagnosed, and current is not supplied to defective interconnections, which may be broken, short-circuited, or unstable. Since current is not supplied to defective interconnections, the interconnections are prevented from becoming unduly heated, and hence electric power consumption of the electronic cassette 20 is minimized.

If an environmental disturbance value is equal to or greater than a threshold value or if dropping of the electronic cassette 20 is detected, then an idle exposure process is carried out, and the electronic cassette 20 is self-diagnosed for a second unimageable region in which an image cannot be captured from the radiation 16, based on image data generated by the idle exposure process. Therefore, an unimageable region, which cannot be ascertained by an actual image capturing process, can be detected.

Since a limited function of the electronic cassette 20 is displayed on the display unit 154, the user can recognize the limited function. If an environmental disturbance value is equal to or greater than a threshold value or if dropping of the electronic cassette 20 is detected, then image-capturing radiation 16 is inhibited from being applied until the fault diagnostic process carried out by the fault diagnosing section 132 is finished. Consequently, the subject 14 is prevented from being unduly exposed to radiation 16.

The first embodiment described above can be modified in the following ways.

Modification 1

In the first embodiment, if a second unimageable region is diagnosed by the real-image diagnosing section 142, then in step S8, a function of the electronic cassette 20 is limited so as not to produce an image in the second unimageable region. However, it is possible that a function of the electronic cassette 20 may not be limited. If a function of the electronic cassette 20 is not limited, then step S8 may be dispensed with, and in step S9, the diagnosed second unimageable region simply is displayed on the display unit 154. At this time, the first unimageable region may also be displayed along with the second unimageable region.

Modification 2

In the first embodiment, both the self-diagnostic process and the real-image diagnostic process are performed. However, either one of the self-diagnostic process or the real-image diagnostic process may be performed.

Modification 3

A display panel, such as a liquid crystal panel or the like, may be disposed on a reverse side of the panel unit 40, i.e., a surface thereof remote from the image capturing surface 46, and an unimageable region diagnosed by the self-diagnostic process or the real-image diagnostic process may be displayed on the display panel on the reverse side of the panel unit 40. Then, simply by turning over the panel unit 40, the user can intuitively recognize which region is an unimageable region. Light-emitting elements such as LEDs or the like may be placed at positions of the region graduations on the electronic cassette 20, and the cassette controller 84 may turn the light-emitting elements on and off in order to indicate an unimageable region.

Modification 4

Figure 10:
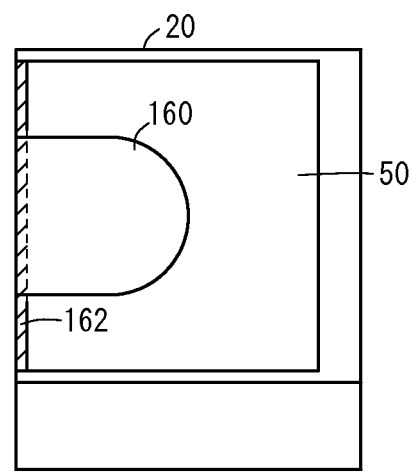
FIG. 10 is a plan view showing the manner in which a radiographic image of a breast is captured by the electronic cassette.

In mammography, it is important to capture images of the armpits because cancer often occurs in the armpits. As shown in FIG. 10, in mammography, an image of the breast 160 is captured while the breast 160 is placed on the panel unit 40 of the electronic cassette 20. Among the end areas of the imageable region 50, one end area 162 near the breast wall serves as a region for capturing an image of the armpit. However, if the end area 162 of the electronic cassette 20 near the breast wall is detected as an unimageable region, then an image of the armpit cannot be captured. If the end area 162 of the imageable region 50 is diagnosed as being an unimageable region by the self-diagnostic process and the real-image diagnostic process, then the function limiter 134 limits a mammographic function. In this case, for example, the user operates the input unit 150 of the console 24 to select an image capturing order from among a plurality of image capturing orders. At this time, the function limiter 134 may limit the types of available image capturing processes, so that a mammographic image capturing order cannot be selected via the console 24.

Modification 5

The real-image diagnosing section 142 diagnoses an unimageable region based on image data generated by the idle exposure process. However, the real-image diagnosing section 142 may diagnose an unimageable region based on image data that is generated by a blank reading process. Such a blank reading process refers to a process in which radiation 16 is not applied to the electronic cassette 20, and electric signals stored in the pixels 104, i.e., electric signals representative of dark current, are read.

Modification 6

In the first embodiment, the radiation detector 56 includes on a single substrate, e.g., a glass substrate, a single radiation conversion panel 54 including the TFTs 102 and the pixels 104. According to Modification 6, the radiation detector 56 includes on a substrate a plurality of respective radiation conversion panels 54, each of which includes a plurality of TFTs 102 and a plurality of pixels 104. The radiation conversion panels 54, which are bonded together without gaps therebetween, convert phosphorescence generated by the scintillator 52 into electric signals. The radiation conversion panels 54 collectively are capable of producing a single radiographic image. According to Modification 6, the operation sequence according to the flowchart shown in FIG. 9 is performed with respect to each of the radiation conversion panels 54, thereby managing each of the radiation conversion panels 54.

Modification 7

In the first embodiment, the TFTs 102 and the pixels 104 of the radiation conversion panel 54 are disposed on a single substrate, e.g., a glass substrate. According to Modification 7, a single radiation conversion panel 54 is produced by forming a plurality of TFTs 102 and a plurality of pixels 104 on each of a plurality of substrates, i.e., silicon wafers, and thereafter bonding the substrates together.

Modification 8

Modifications 1 through 7 may be combined together insofar as they do not counteract one another or operate in a contradictory manner.

Second Embodiment

Parts and features according to a second embodiment, which differ from those according to the first embodiment, will be described below, whereas identical parts and features will not be described. More specifically, the radiographic image capturing system 10, and the radiation device 18, the electronic cassette 20, the console 24, the display device 26, the RIS 28, the HIS 30, and the server 32 according to the second embodiment are identical to those of the first embodiment, however, the electronic cassette 20 has an electric configuration that differs from that of the electronic cassette 20 according to the first embodiment.

Figure 11:
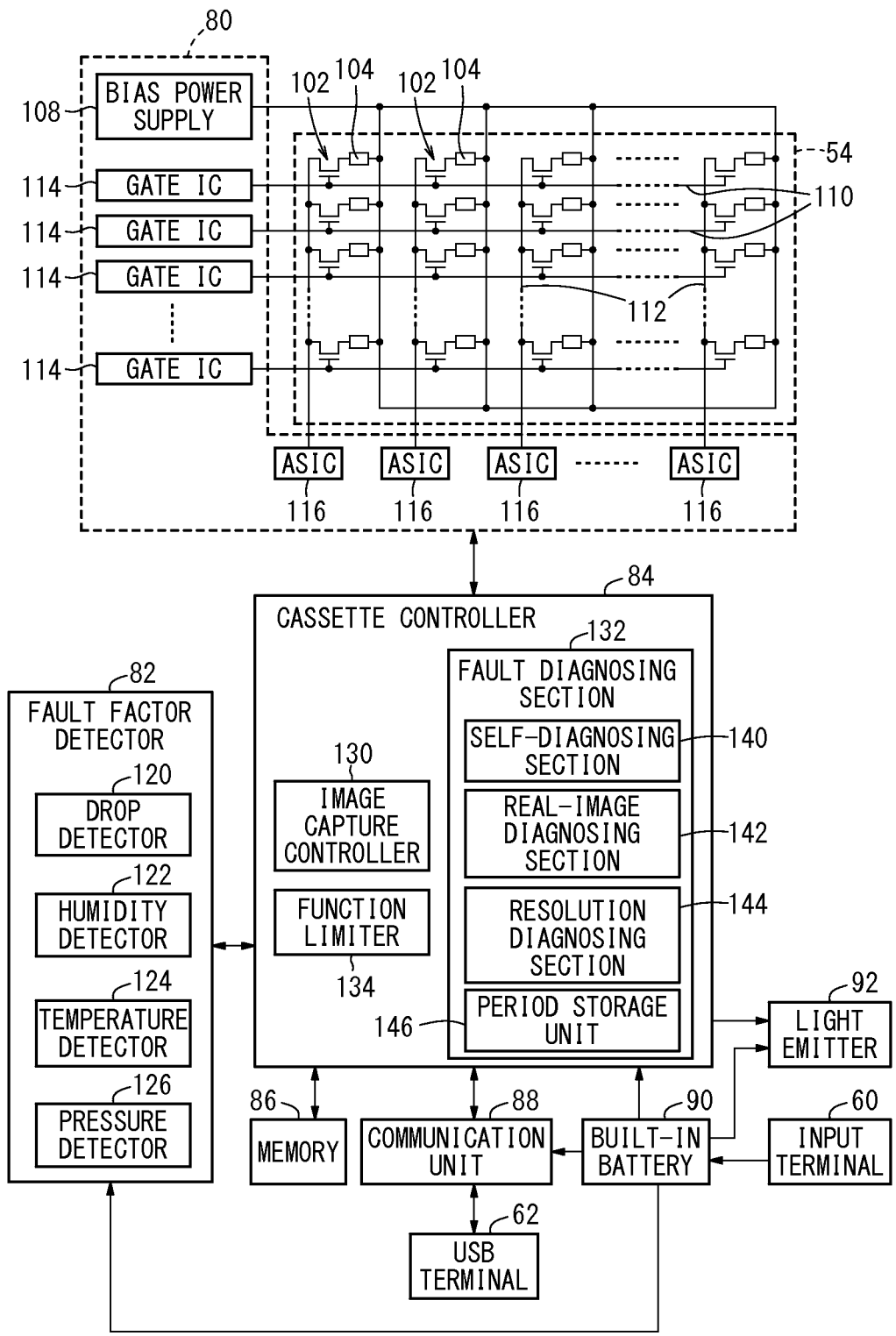
FIG. 11 is an electric block diagram of an electronic cassette according to a second embodiment of the present invention.

FIG. 11 is an electric block diagram of the electronic cassette 20 according to the second embodiment. The electronic cassette 20 has a cassette controller 84, including a fault diagnosing section 132 which differs from the fault diagnosing section 132 according to the first embodiment. According to the second embodiment, the fault diagnosing section 132 periodically performs a first fault diagnosing process. If dropping of the electronic cassette 20 is detected, or if a detected external pressure is equal to or greater than a threshold value, then the fault diagnosing section 132 performs the first fault diagnosing process at reduced intervals, i.e., in reduced periodic cycles. The fault diagnosing section 132 also performs a second fault diagnosing process along with the first fault diagnosing process. The first fault diagnosing process includes a self-diagnostic process and a real-image diagnostic process. The second fault diagnosing process includes a resolution diagnostic process.

The fault diagnosing section 132 includes a self-diagnosing section 140 that performs a first fault diagnosing process, a real-image diagnosing section 142 that performs a second fault diagnosing process, a resolution diagnosing section 144 that performs a resolution diagnostic process, and a period storage unit 146, which stores respective periodic cycles of the periodic diagnostic process. The period storage unit 146 stores periods for each of the periodic cycles as default values. The fault diagnosing section 132 periodically performs the first fault diagnosing process in respective periodic cycles, the periods of which have been stored in the period storage unit 146. Components of the fault diagnosing section, which have the same functions as those according to the first embodiment, are denoted by identical reference characters.

The resolution diagnosing section 144 diagnoses the resolution of an image based on image data generated by an idle exposure process, in which the radiation 16 that has passed through a resolution test chart, e.g., an MTF chart, is detected and converted into an image.

Operations of the electronic cassette 20 according to the second embodiment will be described below with reference to the flowcharts shown in FIGS. 12 and 13. The fault factor detector 82 periodically detects dropping of the electronic cassette 20, environmental humidity values, environmental temperature values, and external pressure values.

Figure 12:
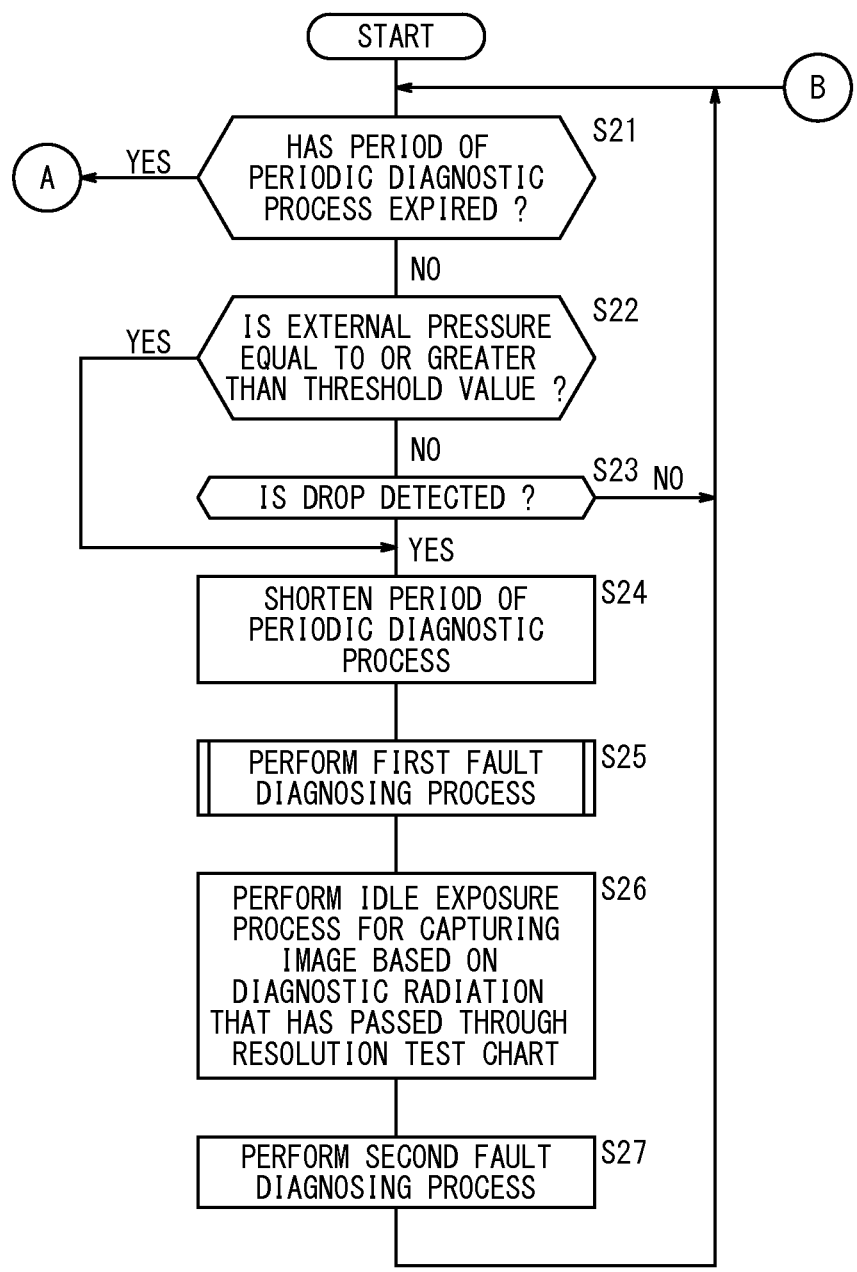
FIG. 12 is a flowchart of an operation sequence of the electronic cassette according to the second embodiment.

The fault diagnosing section 132 judges whether or not the period of each of the periodic cycles of the periodic diagnostic process, which is stored in the period storage unit 146, has expired (step S21 of FIG. 12). For example, if the period stored in the period storage unit 146 is 6 months, then the fault diagnosing section 132 judges whether or not 6 months have elapsed from a previous periodic diagnostic process.

If the fault diagnosing section 132 decides that the period of each of the periodic cycles of the periodic diagnostic process has not arrived in step S21, then the fault diagnosing section 132 judges whether or not an external pressure detected by the pressure detector 126 is equal to or greater than a threshold value (step S22).

If the fault diagnosing section 132 decides that the external pressure is not equal to or greater than the threshold value, then the fault diagnosing section 132 judges whether or not the drop detector 120 has detected dropping of the electronic cassette 20 (step S23). If the fault diagnosing section 132 judges that the drop detector 120 has not detected dropping of the electronic cassette 20 in step S23, then control returns to step S21.

If the fault diagnosing section 132 decides that the external pressure is equal to or greater than the threshold value in step S22, or if the fault diagnosing section 132 decides that the drop detector 120 has detected dropping of the electronic cassette 20 in step S23, then the fault diagnosing section 132 decides that the electronic cassette 20 has malfunctioned or has suffered from a fault (for example, the columnar crystalline structure 72 or the humidity-resistant protector 74 has become broken or cracked, or a gate IC 114 or the like has become broken, or an interconnection is broken or short-circuited). In this case, the fault diagnosing section 132 shortens the period of the periodic diagnostic process by a predetermined period (e.g., 1 month) or a predetermined percent (e.g., 70 percent) (step S24). More specifically, if an external pressure, which is equal to or greater than the threshold value, is detected, or if dropping of the electronic cassette 20 is detected, the electronic cassette 20 is considered to deteriorate quickly. Therefore, the fault diagnosing section 132 shortens the period of the periodic diagnostic process. If the present period of the periodic diagnostic process is 6 months, then after being shortened by 1 month, the period of the periodic diagnostic process becomes 5 months. The shortened period of the periodic diagnostic process is stored in the period storage unit 146. The fault diagnosing section 132 stores information indicating that an external pressure, which is equal to or greater than the threshold value, has been detected, or that dropping of the electronic cassette 20 has been detected, in a non-illustrated internal memory.

Then, the fault diagnosing section 132 performs a first fault diagnosing process by carrying out a self-diagnostic process and a real-image diagnostic process (step S25). The fault diagnosing section 132 performs the first fault diagnosing process since functions of the electronic cassette 20 may possibly have become impaired in a case where the external pressure, which was equal to or greater than the threshold value, or dropping of the electronic cassette 20 was detected. The first fault diagnosing process will be described in detail later.

Then, the image capture controller 130 performs an idle exposure process for capturing an image based on the diagnostic radiation 16 that has passed through a resolution test chart (step S26). More specifically, the image capture controller 130 outputs a request signal to the console 24 through the communication unit 88 for requesting application of diagnostic radiation 16. In response to the request signal, the console 24 outputs a command signal to the radiation device 18 for applying diagnostic radiation 16. When the console 24 outputs the command signal, it controls the display unit 154 to display the letters "SET RESOLUTION TEST CHART", thereby prompting the user to set a resolution test chart.

In response to the command signal, the radiation device 18 applies diagnostic radiation 16 after the elapse of a given period of time, e.g., 3 minutes. Before the given period of time elapses, the user sets a resolution test chart on the image capturing surface 46 of the electronic cassette 20. After having output the request signal, the image capture controller 130 controls the pixels 104 so as to be exposed to diagnostic radiation 16 in a predetermined time exposure process after the elapse of the given period of time. Then, the image capture controller 130 reads the electric charges stored in the pixels 104 by the time exposure process.

After having acquired image data from diagnostic radiation 16 that has passed through the resolution test chart, the fault diagnosing section 132 performs a resolution diagnostic process to thereby carry out a second fault diagnosing process (step S27). More specifically, the resolution diagnosing section 144 diagnoses an image resolution based on the image data captured in step S26. In this manner, the image resolution, which may have been lowered due to the scintillator 52 having become broken or cracked, can be detected. The resolution diagnosing section 144 sends the result of the resolution diagnostic process to the console 24 through the communication unit 88. The console 24 displays the result of the resolution diagnostic process from the resolution diagnosing section 144 on the display unit 154, thereby indicating the result to the user. After the second fault diagnosing process in step S27, control returns to step S21. The above operation sequence is repeated until the period of the periodic diagnostic process expires.

If the fault diagnosing section 132 decides that the period of the periodic diagnostic process has expired in step S21, then the fault diagnosing section 132 performs a first fault diagnosing process by carrying out a self-diagnostic process and a real-image diagnostic process (step S28). By periodically performing the first fault diagnosing process, the fault diagnosing section 132 can periodically diagnose the electronic cassette 20 for a fault or malfunction. Since subjects, who are patients, are placed on the electronic cassette 20, the electronic cassette 20 experiences external pressures and stresses in a case where the electronic cassette 20 is in normal use. Therefore, the electronic cassette 20 tends to suffer from a fault or malfunction under such external pressures and stresses while in continuous use.

Then, the fault diagnosing section 132 judges whether or not an external pressure equal to or greater than the threshold value, or dropping of the electronic cassette 20 has been detected thus far (step S29). If in step S29, the fault diagnosing section 132 decides that an external pressure equal to or greater than the threshold value, or dropping of the electronic cassette 20 has not been detected thus far, control returns to step S21 of FIG. 12.

If in step S29, the fault diagnosing section 132 decides that an external pressure equal to or greater than the threshold value, or dropping of the electronic cassette 20 has been detected thus far, the image capture controller 130 performs an idle exposure process for capturing an image based on diagnostic radiation 16 that has passed through a resolution test chart (step S30). In step S30, the image capture controller 130 operates in the same manner as in step S26, thereby capturing an image based on diagnostic radiation 16 that has passed through the resolution test chart.

Thereafter, the fault diagnosing section 132 performs a resolution diagnostic process based on the captured image data to carry out a second fault diagnosing process (step S31). Then, control returns to step S21 of FIG. 12. In this manner, image resolution, which may have become lowered as a result of deliquescing of the scintillator 52, can be detected. The resolution diagnosing section 144 sends the results of the resolution diagnostic process to the console 24 through the communication unit 88. The console 24 displays the results of the resolution diagnostic process from the resolution diagnosing section 144 on the display unit 154, thereby indicating such results to the user. If an external pressure equal to or greater than the threshold value, or dropping of the electronic cassette 20 has been detected thus far, the second fault diagnosing process is added to the periodic diagnostic process, because a sign of deterioration of the electronic cassette 20 due to an excessive external pressure being applied thereto, or as a result of dropping thereof, can accurately be grasped, thereby enhancing the accuracy with which the electronic cassette 20 is diagnosed, and improving the prediction of the time at which the electronic cassette should be replaced. Therefore, if an external pressure equal to or greater than the threshold value has not been applied to the electronic cassette 20, or the electronic cassette 20 has not been dropped thus far, the humidity-resistant protector 74 is not likely to have cracked or fractured, thereby making it less likely that the scintillator 52 has been exposed to humidity.

Figure 14:
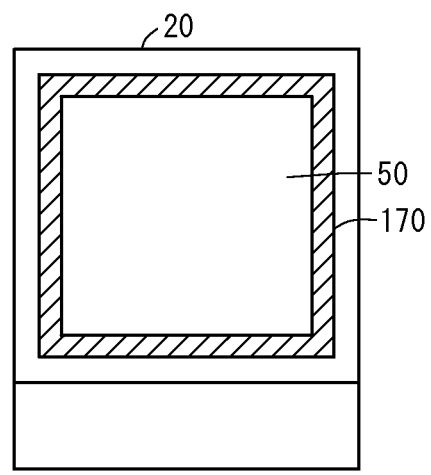
FIG. 14 is a diagram showing a peripheral edge region of an imageable region, which is not used for image formation.

In particular, the columnar crystalline structure 72 is highly subject to deterioration, thus resulting in reduced resolution due to exposure to humidity. Therefore, in the second fault diagnosing process, the idle exposure process is carried out using a resolution test chart. As shown in FIG. 14, the second fault diagnosing process may use a peripheral edge region 170 of the imageable region 50. Electric charges stored in the pixels 104 and belonging to the peripheral edge region 170 are not used for image formation, i.e., are dumped during image formation. However, since the scintillator 52 starts to deteriorate due to humidity from the peripheral edge region thereof, the second fault diagnosing process can make use of the peripheral edge region 170 of the imageable region 50 for quickly grasping a sign of deterioration of the electronic cassette 20.

While the fault diagnosing section 132 carries out the first fault diagnosing process and the second fault diagnosing process, the fault diagnosing section 132 sends an irradiation inhibit signal to the console 24 through the communication unit 88 in order to prevent the radiation device 18 from applying image-capturing radiation 16. In response to the irradiation inhibit signal, the console 24 sends an irradiation inhibit command to the radiation device 18. Accordingly, while the first fault diagnosing process and the second fault diagnosing process are carried out, the radiation device 18 is inhibited from applying image-capturing radiation 16. In the event of failure of the communication unit 88, since the console 24 is unable to communicate wirelessly with the electronic cassette 20, the console 24 diagnoses the communication unit 88 as failing, and may also inhibit the communication unit 88 from applying image-capturing radiation 16. When the fault diagnosing section 132 has finished the first fault diagnosing process and the second fault diagnosing process, the fault diagnosing section 132 sends a signal to the console 24 indicating that image-capturing radiation 16 can be applied. In response to such a signal, the console 24 sends information indicating that image-capturing radiation 16 can be applied to the radiation device 18. Thus, the radiation device 18 is rendered capable of applying image-capturing radiation 16.

Figure 15:
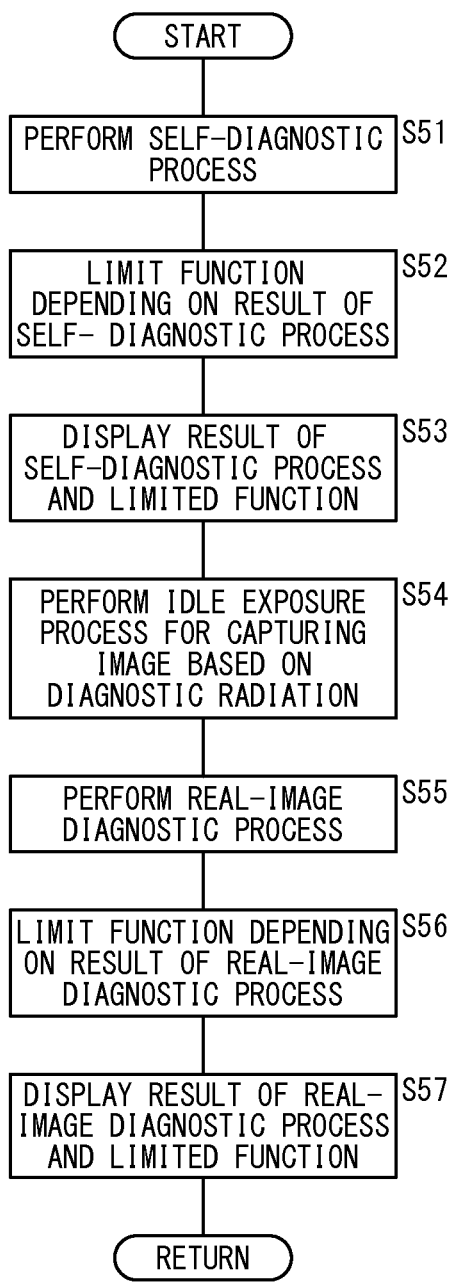
FIG. 15 is a flowchart of a first fault diagnosing process according to the second embodiment.

FIG. 15 is a flowchart of the first fault diagnosing process. When the first fault diagnosing process is started, the self-diagnosing section 140 carries out a self-diagnostic process (step S51). More specifically, the self-diagnosing section 140 diagnoses the gate ICs 114 and the ASICs 116 for a fault, diagnoses the interconnections, and diagnoses the panel unit 40 for an unimageable region. The self-diagnosing section 140 also diagnoses the memory 86, the communication unit 88, and the built-in battery 90. The self-diagnosing section 140 sends the results of the self-diagnostic process to the console 24 through the communication unit 88. In step S51, the self-diagnosing section 140 operates in the same manner as in step S3 of FIG. 9.

Then, the function limiter 134 limits functions of the electronic cassette 20, which is in continuous use, depending on the results of the self-diagnostic process in step S52. For example, if the self-diagnosing section 140 diagnoses a gate IC 114 or an ASIC 116 as suffering from a fault, then the function limiter 134 stops supplying electric power to the faulty gate IC 114 or to the faulty ASIC 116. Thus, an image capturing process in the unimageable region is limited. The function limiter 134 also stops supplying electric power to an interconnection, which has been diagnosed as being broken, short-circuited, or unstable. The function limiter 134 sends information to the console 24 through the communication unit 88 concerning the function that was limited depending on the results of the self-diagnostic process. The unimageable region, which is diagnosed by the self-diagnostic process, will be referred to as a first unimageable region. In step S52, the function limiter 134 operates in the same manner as in step S4 of FIG. 9.

Then, the controller 152 of the console 24 controls the display unit 154 to display the results of the self-diagnostic process and the function that was limited depending on the results of the self-diagnostic process (step S53). For example, if a gate IC 114 for reading the electric charges stored in the pixels 104 of the row indicated by a region corresponding to graduation A on the image capturing surface 46, and an ASIC 116 for reading the electric charges stored in the pixels 104 of the column indicated by a region corresponding to graduation 1 on the image capturing surface 46 are diagnosed as being faulty, then, as shown in FIG. 8, the diagnosed first unimageable region in the imageable region 50' of the electronic cassette 20' is displayed in hatching, and the message "IMAGING REGION OF COLUMN 1 AND ROW A IS AN UNIMAGEABLE REGION" is displayed in the explanation field. If the built-in battery 90 is diagnosed as having a remaining stored energy level lower than a predetermined value, then the message "BUILT-IN BATTERY IS SUFFERING CAPACITY SHORTAGE. CONNECT CABLE AS BUILT-IN BATTERY IS LIMITED" is displayed in the explanation field. In step S53, the controller 152 operates in the same manner as in step S5 of FIG. 9.

Then, the image capture controller 130 performs an idle exposure process using diagnostic radiation 16 (step S54). More specifically, the image capture controller 130 outputs a request signal to the console 24 through the communication unit 88 for requesting application of diagnostic radiation 16. In response to the request signal, the console 24 outputs to the radiation device 18 a command signal for applying diagnostic radiation 16. In response to the command signal, the radiation device 18 applies diagnostic radiation 16. After having output the request signal, the image capture controller 130 controls the radiation conversion panel 54 so as to be exposed to diagnostic radiation 16 for a given period of time, and then reads the electric charges that are stored in the pixels 104 as a result of being exposed to diagnostic radiation 16. Image data, which are converted from the electric charges generated as a result of being exposed to diagnostic radiation 16, are stored in the memory 86. At this time, image data are produced based on the diagnostic radiation 16, while the function is limited depending on the results of the self-diagnostic process. In step S54, the image capture controller 130 operates in the same manner as in step S6 of FIG. 9.

Then, based on the image data produced from the diagnostic radiation 16, the real-image diagnosing section 142 performs a real-image diagnostic process for diagnosing the electronic cassette 20 for an unimageable region in which an image cannot be captured (step S55). The unimageable region, which is detected by the real-image diagnosing section 142, is referred to as a second unimageable region. The real-image diagnosing section 142 sends the results of the real-image diagnostic process to the console 24 through the communication unit 88. In step S55, the real-image diagnosing section 142 operates in the same manner as in step S7 shown in FIG. 9.

Then, the function limiter 134 limits the function of the electronic cassette 20, which is in continuous use, depending on the results of the real-image diagnostic process (step S56). In other words, the function limiter 134 limits the function of the electronic cassette 20 so that an image will not be acquired from the unimageable region that was detected by the real-image diagnosing section 142. For example, the function limiter 134 may inhibit electric power from being supplied to gate ICs 114 and ASICs 116, so as not to read electric charges stored in pixels 104 that belong to the diagnosed second unimageable region. Alternatively, the function limiter 134 may trim the image data generated based on the radiation 16, so as to remove such image data from the second unimageable region. The function limiter 134 sends information to the console 24 through the communication unit 88 concerning the function that was limited depending on the result of the real-image diagnostic process. In step S56, the function limiter 134 operates in the same manner as in step S8 of FIG. 9.

Then, the controller 152 of the console 24 controls the display unit 154 in order to display the function that was limited depending on the results of the real-image diagnostic process, and the function that was limited depending on the results of the real-image diagnostic process (step S57). In the same manner as shown in FIG. 8, the controller 152 may control the display unit 154 to display the second unimageable region that was diagnosed by the real-image diagnostic process. If an image capturing area is limited by inhibiting electric power from being supplied to the gate ICs 114, which read the stored electric charges from pixels 104 in the second unimageable region, then the actually limited image capturing area becomes wider than, and hence is not in agreement with, the second unimageable region. In this case, the actually limited image capturing area, rather than the second unimageable region, is displayed as an unimageable region. The function that was limited depending on the results of the real-image diagnostic process may be displayed along with the function that was limited depending on the results of the self-diagnostic process. For example, the first unimageable region and the second unimageable region may be displayed together. In step S57, the controller 152 operates in the same manner as in step S9 shown in FIG. 9.

As described above, the first fault diagnosing process is carried out periodically. If an external pressure, which is equal to or greater than the threshold value is detected, or if dropping of the electronic cassette 20 is detected, then the first fault diagnosing process is performed, and the intervals at which the first fault diagnosing process is carried out are shortened periodically. Consequently, the degree to which the electronic cassette 20 deteriorates over time can accurately be diagnosed. The results of the diagnostic process, which are sent from the console 24 to the server 32, allows the maintenance provider to predict a timing at which a replacement electronic cassette 20 should be purchased, as well as a timing at which parts of the electronic cassette 20 should be replaced.

If an external pressure, which is equal to or greater than the threshold value, is detected, or if dropping of the electronic cassette 20 is detected, then the second fault diagnosing process for diagnosing image resolution is subsequently carried out along with the first fault diagnosing process. Accordingly, the degree to which the resolution of the electronic cassette 20 has decreased can be diagnosed accurately.

The results of the diagnostic process are displayed on the display unit 154, thereby allowing the user to recognize the degree to which the electronic cassette 20 has deteriorated at present.

Inasmuch as the function of the electronic cassette 20 is limited depending on the results of the diagnostic process, the electronic cassette 20 is prevented from becoming unduly heated, and hence electric power consumption of the electronic cassette 20 is minimized. While the fault diagnosing section 132 is performing a diagnostic process, the radiation device 18 is inhibited from applying image-capturing radiation 16, so that the subject 14 is prevented from being unduly exposed to radiation 16 during the diagnostic process.

The second embodiment described above can be modified in the following ways.

Modification 1

In the second embodiment, if an external pressure is equal to or greater than the threshold value, or if dropping of the electronic cassette 20 is detected (YES in step S22 or YES in step S23 of FIG. 12), control proceeds to step S24. However, if either one of a detected external pressure, a detected environmental humidity value, a detected environmental temperature value, and a detected temperature change is equal to or greater than a threshold value, or if dropping of the electronic cassette 20 is detected, then control may proceed to step S24. This is because the electronic cassette 20 may possibly be suffering from a fault due to the environmental temperature or the environmental humidity. In this case, in step S29 of FIG. 13, the fault diagnosing section 132 judges whether or not an external pressure, an environmental humidity value, an environmental temperature, or a temperature change is equal to or greater than a threshold value, or if dropping of the electronic cassette 20 has been detected thus far. If the fault diagnosing section 132 decides that an external pressure, an environmental humidity value, an environmental temperature, or a temperature change is equal to or greater than a threshold value, or that dropping of the electronic cassette 20 has been detected, then control proceeds to step S30. If the fault diagnosing section 132 decides that an external pressure, an environmental humidity value, an environmental temperature, or a temperature change is not equal to or greater than a threshold value, or that dropping of the electronic cassette 20 has not been detected, then control returns to step S21 of FIG. 21.

Modification 2

In the second embodiment, if an external pressure is equal to or greater than the threshold value, or if dropping of the electronic cassette 20 is detected, then the fault diagnosing section 132 performs the first fault diagnosing process and the second fault diagnosing process (step S25 and step S27 of FIG. 12). However, the fault diagnosing section 132 need not necessarily perform the second fault diagnosing process. If the fault diagnosing section 132 does not perform the second fault diagnosing process, then control goes from step S25 back to step S21. In this case, steps S26, S27 are no longer required, since image resolution is highly likely not to have decreased significantly immediately after an external pressure was detected, which is equal to or greater than the threshold value, or immediately after dropping of the electronic cassette 20 was detected.

Modification 3

In the second embodiment, if an external pressure is equal to or greater than the threshold value, or if dropping of the electronic cassette 20 is detected (YES in step S22 or YES in step S23 of FIG. 12), the period of the periodic diagnostic process is shortened. However, if the present period of the periodic diagnostic process is equal to or smaller than a predetermined amount (e.g., 1 month, 15 days, or the like), then the period of the periodic diagnostic process may not be shortened further. Since the electronic cassette 20 cannot be used during the periodic diagnostic process, the above limitation on shortening of the period is effective to prevent patient diagnoses from being adversely affected by overly frequent repetitions of the periodic diagnostic process, e.g., ones that are performed each day.

Modification 4

Figure 13:
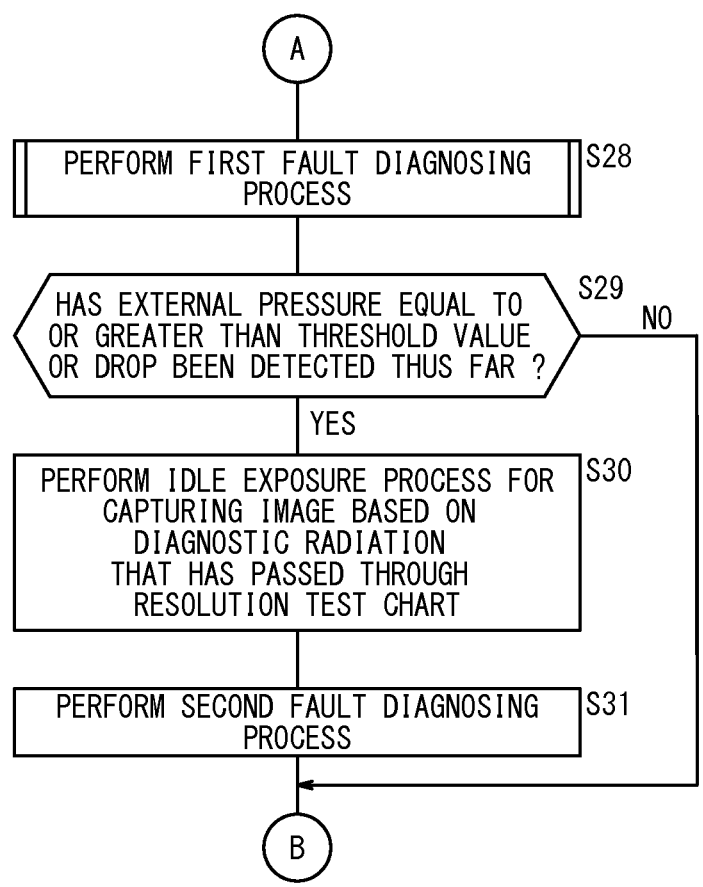
FIG. 13 is another flowchart of the operation sequence of the electronic cassette according to the second embodiment.

In the second embodiment, if an external pressure equal to or greater than the threshold value, or dropping of the electronic cassette 20 has been detected thus far, the second fault diagnosing process is carried out as part of the periodic diagnostic process along with the first fault diagnosing process (steps S29 through S31 of FIG. 13). However, even if an external pressure equal to or greater than the threshold value, or dropping of the electronic cassette 20 has been detected thus far, the second fault diagnosing process may not be carried out. If the second fault diagnosing process is not carried out, then steps S29 through S31 are no longer required, and control goes from step S28 back to step S21 of FIG. 12. The resolution diagnostic process may be included as part of the first fault diagnosing process.

Modification 5

According to Modification 5, if a detected external pressure, environmental humidity, environmental temperature, or temperature change is equal to or greater than a predetermined value, or if the fault diagnosing section 132 counts the number of times that the detected external pressure, the environmental humidity, the environmental temperature, or the temperature change is equal to or greater than the predetermined value, and the counted number exceeds a predetermined number, then the fault diagnosing section 132 shortens the period of the periodic diagnostic process. In such a situation, since the electronic cassette 20 is considered to deteriorate quickly, the period of the periodic diagnostic process is shortened.

The fault diagnosing section 132 may operate according to Modification 5 after having detected an external pressure equal to or greater than the threshold value, or after having detected dropping of the electronic cassette 20. Alternatively, the fault diagnosing section 132 may operate according to Modification 5 regardless of whether an external pressure equal to or greater than the threshold value or dropping of the electronic cassette 20 has been detected.

Modification 6

In the second embodiment, the image capture controller 130 captures two images based on application of diagnostic radiation 16 for performing a real-image diagnosis and a resolution diagnosis, respectively. However, the image capture controller 130 may capture only a single image from the diagnostic radiation 16. If the image capture controller 130 captures a single image from the diagnostic radiation 16, then the fault diagnosing section 132 performs a real-image diagnosis and a resolution diagnosis using image data of the captured signal image. More specifically, the fault diagnosing section 132 captures an image from the fault diagnosing section 132 that has been passed through a resolution test chart, and the fault diagnosing section 132 performs both real-image diagnosis and resolution diagnosis using the image data of the captured image.

Modification 7

In the second embodiment, both a self-diagnostic process and a real-image diagnostic process are carried out as the first fault diagnosing process. However, either one of a self-diagnostic process and a real-image diagnostic process may be carried out. Alternatively, a different diagnostic process, other than a self-diagnostic process and a real-image diagnostic process, may be carried out as the first fault diagnosing process. Although according to the second embodiment, a resolution diagnostic process is carried out as the second fault diagnosing process, another diagnostic process may be carried out in addition to or instead of the resolution diagnostic process.

Modification 8

In the second embodiment, if the real-image diagnosing section 142 diagnoses a second unimageable region, then the function of the electronic cassette 20 is limited in step S56 of FIG. 15 so as not to produce an image in the second unimageable region. However, the function of the electronic cassette 20 may not be limited. If the function of the electronic cassette 20 is not limited, then steps S56, S57 are dispensed with, and instead of steps S56 and S57, the second unimageable region is displayed on the display unit 154.

Modification 9

A display panel such as a liquid crystal panel or the like may be disposed on the reverse side of the panel unit 40, i.e., a surface thereof remote from the image capturing surface 46, and an unimageable region diagnosed by the self-diagnostic process or the real-image diagnostic process may be displayed on the display panel, which is provided on the reverse side of the panel unit 40. Thus, the user can intuitively recognize which region is an unimageable region simply by turning the panel unit 40 over. Light-emitting elements, such as LEDs or the like, may be placed at positions corresponding to the region graduations on the electronic cassette 20, and the cassette controller 84 may turn such light-emitting elements on and off in order to indicate an unimageable region.

Modification 10

The real-image diagnosing section 142 diagnoses an unimageable region based on image data generated by the idle exposure process. However, the real-image diagnosing section 142 may diagnose an unimageable region based on image data that is generated by a blank reading process. Such a blank reading process refers to a process in which radiation 16 is not applied to the electronic cassette 20, and electric signals stored in the pixels 104, i.e., electric signals representative of dark current, are read.

Modification 11

In mammography, it is important to capture images of the armpits because cancer often occurs in the armpits. As shown in FIG. 10, in mammography, an image of the breast 160 is captured while the breast 160 is placed on the panel unit 40 of the electronic cassette 20. Among the end areas of the imageable region 50, one end area 162 near the breast wall serves as a region for capturing an image of the armpit. However, if the end area 162 of the electronic cassette 20 near the breast wall is detected as an unimageable region, then an image of the armpit cannot be captured. If the end area 162 of the imageable region 50 is diagnosed as being an unimageable region by the self-diagnostic process and the real-image diagnostic process, then the function limiter 134 limits a mammographic function. In this case, for example, the user operates the input unit 150 of the console 24 to select an image capturing order from among a plurality of image capturing orders. At this time, the function limiter 134 may limit the types of available image capturing processes, so that a mammographic image capturing order cannot be selected via the console 24.

Modification 12

Figure 16:
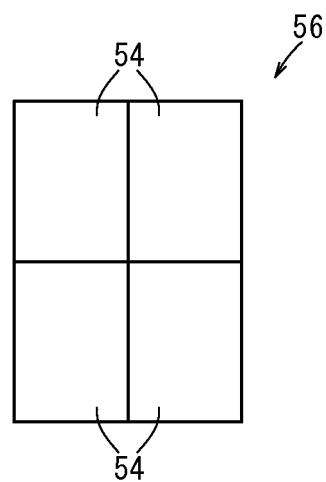
FIG. 16 is a view showing a layout structure of a radiation conversion panel of a radiation detector according to a twelfth modification.

In the second embodiment, the radiation detector 56 includes on a single substrate, e.g., a glass substrate, a single radiation conversion panel 54 including the TFTs 102 and the pixels 104. According to Modification 12, as shown in FIG. 16, the radiation detector 56 includes on a substrate a plurality of respective radiation conversion panels 54, each of which includes a plurality of TFTs 102 and a plurality of pixels 104. The radiation conversion panels 54, which are bonded together without gaps therebetween, convert phosphorescence generated by the scintillator 52 into electric signals. The radiation conversion panels 54 collectively are capable of producing a single radiographic image. According to Modification 12, the operation sequence according to the flowchart shown in FIGS. 12 and 13 is performed with respect to each of the radiation conversion panels 54, thereby managing each of the radiation conversion panels 54.

Modification 13

In the second embodiment, the TFTs 102 and the pixels 104 of the radiation conversion panel 54 are disposed on a single substrate, e.g., a glass substrate. According to Modification 13, a single radiation conversion panel 54 is produced by forming a plurality of TFTs 102 and a plurality of pixels 104 on each of a plurality of substrates, i.e., silicon wafers, and thereafter bonding the substrates together.

Modification 14

Modifications 1 through 13 may be combined together insofar as they do not counteract one another or operate in a contradictory manner.

Although various embodiments of the present invention have been described above, the technical scope of the present invention is not limited by the scope of the respective embodiments. It will be obvious to those skilled in the art that various changes or improvements can be made to each of the above embodiments. It is also apparent from the scope of the patent claims that such changes and improvements are included within the technical scope of the present invention.

The invention claimed is:

1. A diagnostic method for a radiographic image capturing system having a radiation device for applying radiation, and a radiographic image capturing apparatus including an image capturing panel for capturing an image from the applied radiation, the diagnostic method comprising:
   a fault diagnosing step for performing a first fault diagnosing process to periodically diagnose with a fixed period the radiographic image capturing apparatus for a fault; and
   a fault factor detecting step for detecting an external pressure or dropping of the radiographic image capturing apparatus;
   wherein if the detected external pressure is equal to or greater than a threshold value or dropping of the radiographic image capturing apparatus is detected, in the fault diagnosing step, the fixed period is shortened and the first fault diagnosing process is periodically performed.

2. The diagnostic method according to claim 1, wherein the radiation device applies diagnostic radiation for diagnosing the radiographic image capturing apparatus for a fault in the image capturing panel when the first fault diagnosing process is performed; and
   the first fault diagnosing process performed in the fault diagnosing step diagnoses an unimageable region in which an image cannot be captured from the radiation within an entire image capturing area of the image capturing panel, based on image data generated from the diagnostic radiation by an idle exposure process or a blank reading process.

3. The diagnostic method according to claim 2, wherein if the detected external pressure is equal to or greater than the threshold value or dropping of the radiographic image capturing apparatus is detected, in the fault diagnosing step a second fault diagnosing process is performed subsequently periodically along with the first fault diagnosing process.

4. The diagnostic method according to claim 3, wherein the second fault diagnosing process diagnoses a resolution of an image based on image data generated by the idle exposure process using a resolution test chart.

5. The diagnostic method according to claim 1, further comprising:
   an indicating step for indicating, to a user, the results of the first fault diagnosing process performed in the fault diagnosing step.

6. The diagnostic method according to claim 1, wherein if the external pressure, an environmental humidity, an environmental temperature, or a change in the environmental temperature is equal to or greater than a predetermined value, or if the number of times that the external pressure, the environmental humidity, the environmental temperature, or a change in the environmental temperature is equal to or greater than the predetermined value exceeds a predetermined number, in the fault diagnosing step the first fault diagnosing process is periodically performed at shortened intervals.

7. The diagnostic method according to claim 1, further comprising:
   a function limiting step for limiting a function of the radiographic image capturing apparatus based on the results of the first fault diagnosing process performed in the fault diagnosing step.

8. The diagnostic method according to claim 1, wherein the radiographic image capturing apparatus comprises a portable radiographic image capturing apparatus.

9. The diagnostic method according to claim 1, wherein the radiation device inhibits image-capturing radiation from being applied while the first fault diagnosing process is being performed in the fault diagnosing step.

10. A diagnostic method for a radiographic image capturing apparatus including an image capturing panel for capturing an image from applied radiation, comprising:
   a fault diagnosing step for performing a first fault diagnosing process to periodically diagnose with a fixed period the radiographic image capturing apparatus for a fault; and a fault factor detecting step for detecting an external force or dropping of the radiographic image capturing apparatus;

wherein in the fault diagnosing step, the fixed period is shortened and the first fault diagnosing process is periodically performed if the detected external force is equal to or greater than a threshold value or dropping is detected.

11. The diagnostic method according to claim 1, wherein if the detected external pressure is equal to or greater than a threshold value or dropping of the radiographic image capturing apparatus is detected, in the fault diagnosing step, the first fault diagnosing process is performed, and the fixed period is shortened and the first fault diagnosing process is performed periodically.

12. The diagnostic method according to claim 10, wherein in the fault diagnosing step, the first fault diagnosing process is performed, and the fixed period is shortened and the first fault diagnosing process is periodically performed if the detected external force is equal to or greater than a threshold value or dropping is detected.

* * * * *